(12) United States Patent
Huelskamp et al.

(10) Patent No.: US 11,235,163 B2
(45) Date of Patent: Feb. 1, 2022

(54) IMPLANTABLE MEDICAL DEVICE WITH MULTIPLE MODES OF OPERATION

(71) Applicant: CARDIAC PACEMAKERS, INC., St. Paul, MN (US)

(72) Inventors: Paul Huelskamp, St. Paul, MN (US); Robert D. Brock, II, South Saint Paul, MN (US); Brian L. Schmidt, White Bear Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 245 days.

(21) Appl. No.: 16/134,513

(22) Filed: Sep. 18, 2018

(65) Prior Publication Data
US 2019/0099605 A1    Apr. 4, 2019

Related U.S. Application Data

(60) Provisional application No. 62/561,052, filed on Sep. 20, 2017.

(51) Int. Cl.
*A61N 1/372* (2006.01)
*A61N 1/375* (2006.01)
*A61B 5/00* (2006.01)

(52) U.S. Cl.
CPC .......... *A61N 1/37276* (2013.01); *A61B 5/686* (2013.01); *A61N 1/372* (2013.01);
(Continued)

(58) Field of Classification Search
CPC ................ A61N 1/37276; A61N 1/372; A61N 1/37252; A61N 1/37512; A61N 1/3708;
(Continued)

(56) References Cited

U.S. PATENT DOCUMENTS 3,835,864 A    9/1974 Rasor et al.
3,943,936 A    3/1976 Rasor et al.
(Continued)

FOREIGN PATENT DOCUMENTS

AU    2008279789 B2    10/2011
AU    2008329620 B2    5/2014
(Continued)

OTHER PUBLICATIONS

US 8,886,318 B2, 11/2014, Jacobson et al. (withdrawn)
(Continued)

*Primary Examiner* — John R Downey
(74) *Attorney, Agent, or Firm* — Seager, Tufte & Wickhem LLP.

(57) ABSTRACT

An implantable medical device (IMD) with a receiver having a higher power mode and a lower power mode. In the higher power mode, the receiver can receive a communication from an external device and pass the received communication to a controller, and in the lower power mode the receiver may not receive the communication from the external device and pass the received communication to the controller. In some cases, the IMD may include a physiological sensor providing an output to the controller, and the controller may control whether the receiver is in the higher power mode or the lower power mode based at least in part on the output of the physiological sensor.

17 Claims, 15 Drawing Sheets

(52) U.S. Cl.
CPC ....... *A61N 1/3756* (2013.01); *A61N 1/37205* (2013.01); *A61N 1/37211* (2013.01); *A61N 1/37217* (2013.01); *A61N 1/37252* (2013.01); *A61N 1/37512* (2017.08)

(58) Field of Classification Search
CPC .............. A61N 1/3756; A61N 1/37211; A61N 1/37217; A61B 5/686
USPC ................................ 607/30, 32, 60; 600/509
See application file for complete search history.

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| 4,170,999 A | 10/1979 | Allen et al. | |
| RE30,366 E | 8/1980 | Rasor et al. | |
| 4,243,045 A | 1/1981 | Maas | |
| 4,250,884 A | 2/1981 | Hartlaub et al. | |
| 4,256,115 A | 3/1981 | Bilitch | |
| 4,263,919 A | 4/1981 | Levin | |
| 4,310,000 A | 1/1982 | Lindemans | |
| 4,312,354 A | 1/1982 | Walters | |
| 4,323,081 A | 4/1982 | Wiebusch | |
| 4,357,946 A | 11/1982 | Dutcher et al. | |
| 4,365,639 A | 12/1982 | Goldreyer | |
| 4,375,817 A | 3/1983 | Engle et al. | |
| 4,384,505 A | 5/1983 | Cotton, Jr. et al. | |
| 4,387,717 A | 6/1983 | Brownlee et al. | |
| 4,440,173 A | 4/1984 | Hudziak et al. | |
| 4,476,868 A | 10/1984 | Thompson | |
| 4,494,950 A | 1/1985 | Fischell | |
| 4,511,633 A | 4/1985 | Bruno et al. | |
| 4,522,208 A | 6/1985 | Buffet | |
| 4,537,200 A | 8/1985 | Widrow | |
| 4,556,063 A | 12/1985 | Thompson et al. | |
| 4,562,841 A | 1/1986 | Brockway et al. | |
| 4,577,633 A | 3/1986 | Berkovits et al. | |
| 4,587,970 A | 5/1986 | Holley et al. | |
| 4,593,702 A | 6/1986 | Kepski et al. | |
| 4,593,955 A | 6/1986 | Leiber | |
| 4,630,611 A | 12/1986 | King | |
| 4,635,639 A | 1/1987 | Hakala et al. | |
| 4,674,508 A | 6/1987 | DeCote | |
| 4,712,554 A | 12/1987 | Garson | |
| 4,726,380 A | 2/1988 | Vollmann et al. | |
| 4,729,376 A | 3/1988 | DeCote | |
| 4,754,753 A | 7/1988 | King | |
| 4,759,366 A | 7/1988 | Callaghan | |
| 4,776,338 A | 10/1988 | Lekholm et al. | |
| 4,787,389 A | 11/1988 | Tarjan | |
| 4,793,353 A | 12/1988 | Borkan | |
| 4,819,662 A | 4/1989 | Heil et al. | |
| 4,830,006 A | 5/1989 | Haluska et al. | |
| 4,858,610 A | 8/1989 | Callaghan et al. | |
| 4,880,005 A | 11/1989 | Pless et al. | |
| 4,886,064 A | 12/1989 | Strandberg | |
| 4,887,609 A | 12/1989 | Cole | |
| 4,895,151 A | 1/1990 | Grevis et al. | |
| 4,928,688 A | 5/1990 | Mower | |
| 4,949,719 A | 8/1990 | Pless et al. | |
| 4,967,746 A | 11/1990 | Vandegriff | |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,040,534 A | 8/1991 | Mann et al. | |
| 5,058,581 A | 10/1991 | Silvian | |
| 5,078,134 A | 1/1992 | Heilman et al. | |
| 5,107,850 A | 4/1992 | Olive | |
| 5,109,845 A | 5/1992 | Yuuchi et al. | |
| 5,113,859 A | 5/1992 | Funke | |
| 5,113,869 A | 5/1992 | Nappholz et al. | |
| 5,117,824 A | 6/1992 | Keimel et al. | |
| 5,127,401 A | 7/1992 | Grevious et al. | |
| 5,133,353 A | 7/1992 | Hauser | |
| 5,144,950 A | 9/1992 | Stoop et al. | |
| 5,161,527 A | 11/1992 | Nappholz et al. | |
| 5,170,784 A | 12/1992 | Ramon et al. | |
| 5,179,945 A | 1/1993 | Van Hofwegen et al. | |
| 5,188,105 A | 2/1993 | Keimel | |
| 5,193,539 A | 3/1993 | Schulman et al. | |
| 5,193,540 A | 3/1993 | Schulman et al. | |
| 5,228,437 A | 7/1993 | Schroeppel | |
| 5,241,961 A | 9/1993 | Henry | |
| 5,243,977 A | 9/1993 | Trabucco et al. | |
| 5,259,387 A | 11/1993 | DePinto | |
| 5,265,601 A | 11/1993 | Mehra | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,305,760 A | 4/1994 | McKown et al. | |
| 5,312,439 A | 5/1994 | Loeb | |
| 5,312,441 A | 5/1994 | Mader et al. | |
| 5,313,953 A | 5/1994 | Yomtov et al. | |
| 5,314,459 A | 5/1994 | Swanson et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | deCoriolis et al. | |
| 5,354,316 A | 10/1994 | Keimel | |
| 5,370,667 A | 12/1994 | Alt | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A | 4/1995 | Nolan et al. | |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,456,691 A | 10/1995 | Snell | |
| 5,456,692 A | 10/1995 | Smith, Jr. et al. | |
| 5,458,622 A | 10/1995 | Alt | |
| 5,466,246 A | 11/1995 | Silvian | |
| 5,468,254 A | 11/1995 | Hahn et al. | |
| 5,472,453 A | 12/1995 | Alt | |
| 5,480,413 A | 1/1996 | Greenhut et al. | |
| 5,507,782 A | 4/1996 | Kieval et al. | |
| 5,522,866 A | 6/1996 | Fernald | |
| 5,540,727 A | 7/1996 | Tockman et al. | |
| 5,545,186 A | 8/1996 | Olson et al. | |
| 5,545,202 A | 8/1996 | Dahl et al. | |
| 5,560,369 A | 10/1996 | McClure et al. | |
| 5,571,146 A | 11/1996 | Jones et al. | |
| 5,591,214 A | 1/1997 | Lu | |
| 5,620,466 A | 4/1997 | Haefner et al. | |
| 5,620,471 A | 4/1997 | Duncan | |
| 5,634,938 A | 6/1997 | Swanson et al. | |
| 5,649,968 A | 7/1997 | Alt et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,706,823 A | 1/1998 | Wodlinger | |
| 5,709,215 A | 1/1998 | Perttu et al. | |
| 5,720,295 A | 2/1998 | Greenhut et al. | |
| 5,720,770 A | 2/1998 | Nappholz et al. | |
| 5,725,559 A | 3/1998 | Alt et al. | |
| 5,728,154 A | 3/1998 | Crossett et al. | |
| 5,741,314 A | 4/1998 | Daly et al. | |
| 5,741,315 A | 4/1998 | Lee et al. | |
| 5,752,976 A | 5/1998 | Duffin et al. | |
| 5,752,977 A | 5/1998 | Grevious et al. | |
| 5,755,736 A | 5/1998 | Gillberg et al. | |
| 5,755,737 A | 5/1998 | Prieve et al. | |
| 5,759,199 A | 6/1998 | Snell et al. | |
| 5,774,501 A | 6/1998 | Halpern et al. | |
| 5,792,195 A | 8/1998 | Carlson et al. | |
| 5,792,202 A | 8/1998 | Rueter | |
| 5,792,203 A | 8/1998 | Schroeppel | |

(56) References Cited

U.S. PATENT DOCUMENTS

| | | |
|---|---|---|
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Rostami et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,893,882 A | 4/1999 | Peterson et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,931,857 A | 8/1999 | Prieve et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |
| 5,987,352 A | 11/1999 | Klein et al. |
| 5,987,356 A | 11/1999 | DeGroot |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,288 A * | 2/2000 | Bronner ............... H04B 1/26 455/254 |
| 6,026,320 A | 2/2000 | Carlson et al. |
| 6,029,085 A | 2/2000 | Olson et al. |
| 6,041,250 A | 3/2000 | DePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,091,991 A | 7/2000 | Warren |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,330,477 B1 | 12/2001 | Casavant |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,986 B1 | 6/2002 | Sun et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,442,433 B1 | 8/2002 | Linberg |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,106 B2 | 5/2003 | Guck et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,599,250 B2 | 7/2003 | Webb et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,647,434 B1 | 11/2003 | Kamepalli |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,204 B2 | 4/2004 | DeGroot et al. |
| 6,718,212 B2 | 4/2004 | Parry et al. |
| 6,721,597 B1 | 4/2004 | Bardy et al. |
| 6,725,093 B1 | 4/2004 | Ben-Haim et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |

(56) References Cited

U.S. PATENT DOCUMENTS

| | | |
|---|---|---|
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,031,771 B2 | 4/2006 | Brown et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,433 B1 | 8/2007 | Falkenberg et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,565,197 B2 | 7/2009 | Haubrich et al. |
| 7,583,995 B2 | 9/2009 | Sanders |
| 7,584,002 B2 | 9/2009 | Burnes et al. |
| 7,590,455 B2 | 9/2009 | Heruth et al. |
| 7,593,995 B1 | 9/2009 | He et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,720,543 B2 | 5/2010 | Dudding et al. |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |

(56) References Cited

U.S. PATENT DOCUMENTS

| | | |
|---|---|---|
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Fang et al. |
| 7,904,170 B2 | 3/2011 | Harding |
| 7,907,993 B2 | 3/2011 | Ghanem et al. |
| 7,920,928 B1 | 4/2011 | Fang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,036,746 B2 | 10/2011 | Sanders |
| 8,046,079 B2 | 10/2011 | Bange et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,684 B2 | 4/2012 | Ghanem et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,262,578 B1 | 9/2012 | Bharmi et al. |
| 8,265,748 B2 | 9/2012 | Liu et al. |
| 8,265,757 B2 | 9/2012 | Mass et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,437,842 B2 | 5/2013 | Zhang et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,785 B1 | 9/2013 | Crutchfield et al. |
| 8,532,790 B2 | 9/2013 | Griswold |
| 8,538,526 B2 | 9/2013 | Stahmann et al. |
| 8,541,131 B2 | 9/2013 | Lund et al. |

(56) References Cited

U.S. PATENT DOCUMENTS

| | | |
|---|---|---|
| 8,542,131 B2 | 9/2013 | Jahn |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,205 B2 * | 8/2014 | Ecker ............... H04W 52/0229 375/316 |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,468,772 B2 | 10/2016 | Demmer |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,669,230 B2 | 6/2017 | Koop |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,844,675 B2 | 12/2017 | Hareland et al. |

(56) References Cited

U.S. PATENT DOCUMENTS

| | | | |
|---|---|---|---|
| 9,855,414 B2 | 1/2018 | Marshall et al. | |
| 9,855,430 B2 | 1/2018 | Ghosh et al. | |
| 9,855,435 B2 | 1/2018 | Sahabi et al. | |
| 9,861,815 B2 | 1/2018 | Tran et al. | |
| 10,080,887 B2 | 9/2018 | Schmidt et al. | |
| 10,080,888 B2 | 9/2018 | Kelly et al. | |
| 10,080,900 B2 | 9/2018 | Ghosh et al. | |
| 10,080,903 B2 | 9/2018 | Willis et al. | |
| 10,086,206 B2 | 10/2018 | Sambelashvili | |
| 10,118,026 B2 | 11/2018 | Grubac et al. | |
| 10,124,163 B2 | 11/2018 | Ollivier et al. | |
| 10,124,175 B2 | 11/2018 | Berthiaume et al. | |
| 10,130,821 B2 | 11/2018 | Grubac et al. | |
| 10,137,305 B2 | 11/2018 | Kane et al. | |
| 10,201,710 B2 | 2/2019 | Jackson et al. | |
| 10,207,115 B2 | 2/2019 | Echt et al. | |
| 10,207,116 B2 | 2/2019 | Sheldon et al. | |
| 10,226,197 B2 | 3/2019 | Reinke et al. | |
| 10,226,639 B2 | 3/2019 | Zhang | |
| 10,232,182 B2 | 3/2019 | Hareland et al. | |
| 10,265,503 B2 | 4/2019 | Schmidt et al. | |
| 10,265,534 B2 | 4/2019 | Greenhut et al. | |
| 10,271,752 B2 | 4/2019 | Regnier et al. | |
| 10,278,601 B2 | 5/2019 | Greenhut et al. | |
| 10,279,165 B2 | 5/2019 | Seifert et al. | |
| 10,286,221 B2 | 5/2019 | Sawchuk | |
| 10,307,598 B2 | 6/2019 | Ciciarelli et al. | |
| 10,328,274 B2 | 6/2019 | Zhang et al. | |
| 10,342,981 B2 | 7/2019 | Ghosh et al. | |
| 2001/0034487 A1 | 10/2001 | Cao et al. | |
| 2002/0013613 A1 | 1/2002 | Haller et al. | |
| 2002/0032470 A1 | 3/2002 | Linberg | |
| 2002/0035376 A1 | 3/2002 | Bardy et al. | |
| 2002/0035377 A1 | 3/2002 | Bardy et al. | |
| 2002/0035378 A1 | 3/2002 | Bardy et al. | |
| 2002/0035380 A1 | 3/2002 | Rissmann et al. | |
| 2002/0035381 A1 | 3/2002 | Bardy et al. | |
| 2002/0042629 A1 | 4/2002 | Bardy et al. | |
| 2002/0042630 A1 | 4/2002 | Bardy et al. | |
| 2002/0042634 A1 | 4/2002 | Bardy et al. | |
| 2002/0049475 A1 | 4/2002 | Bardy et al. | |
| 2002/0052636 A1 | 5/2002 | Bardy et al. | |
| 2002/0068958 A1 | 6/2002 | Bardy et al. | |
| 2002/0072773 A1 | 6/2002 | Bardy et al. | |
| 2002/0082665 A1 | 6/2002 | Haller et al. | |
| 2002/0091414 A1 | 7/2002 | Bardy et al. | |
| 2002/0095196 A1 | 7/2002 | Linberg | |
| 2002/0099423 A1 | 7/2002 | Berg et al. | |
| 2002/0103510 A1 | 8/2002 | Bardy et al. | |
| 2002/0107545 A1 | 8/2002 | Rissmann et al. | |
| 2002/0107546 A1 | 8/2002 | Ostroff et al. | |
| 2002/0107547 A1 | 8/2002 | Erlinger et al. | |
| 2002/0107548 A1 | 8/2002 | Bardy et al. | |
| 2002/0107549 A1 | 8/2002 | Bardy et al. | |
| 2002/0107559 A1 | 8/2002 | Sanders et al. | |
| 2002/0120299 A1 | 8/2002 | Ostroff et al. | |
| 2002/0173830 A1 | 11/2002 | Starkweather et al. | |
| 2002/0193846 A1 | 12/2002 | Pool et al. | |
| 2003/0009203 A1 | 1/2003 | Lebel et al. | |
| 2003/0028082 A1 | 2/2003 | Thompson | |
| 2003/0040779 A1 | 2/2003 | Engmark et al. | |
| 2003/0041866 A1 | 3/2003 | Linberg et al. | |
| 2003/0045805 A1 | 3/2003 | Sheldon et al. | |
| 2003/0088278 A1 | 5/2003 | Bardy et al. | |
| 2003/0097153 A1 | 5/2003 | Bardy et al. | |
| 2003/0105497 A1 | 6/2003 | Zhu et al. | |
| 2003/0114908 A1 | 6/2003 | Flach | |
| 2003/0144701 A1 | 7/2003 | Mehra et al. | |
| 2003/0187460 A1 | 10/2003 | Chin et al. | |
| 2003/0187461 A1 | 10/2003 | Chin | |
| 2003/0187484 A1* | 10/2003 | Davis | A61N 1/37223 607/60 |
| 2004/0024435 A1 | 2/2004 | Leckrone et al. | |
| 2004/0068302 A1 | 4/2004 | Rodgers et al. | |
| 2004/0087938 A1 | 5/2004 | Leckrone et al. | |
| 2004/0088035 A1 | 5/2004 | Guenst et al. | |
| 2004/0102830 A1 | 5/2004 | Williams | |
| 2004/0127959 A1 | 7/2004 | Amundson et al. | |
| 2004/0133242 A1 | 7/2004 | Chapman et al. | |
| 2004/0142670 A1* | 7/2004 | Ciccarelli | H04B 1/109 455/214 |
| 2004/0147969 A1 | 7/2004 | Mann et al. | |
| 2004/0147973 A1 | 7/2004 | Hauser | |
| 2004/0167558 A1 | 8/2004 | Igo et al. | |
| 2004/0167587 A1 | 8/2004 | Thompson | |
| 2004/0171959 A1 | 9/2004 | Stadler et al. | |
| 2004/0172067 A1 | 9/2004 | Saba | |
| 2004/0172071 A1 | 9/2004 | Bardy et al. | |
| 2004/0172077 A1 | 9/2004 | Chinchoy | |
| 2004/0172104 A1 | 9/2004 | Berg et al. | |
| 2004/0176817 A1 | 9/2004 | Wahlstrand et al. | |
| 2004/0176818 A1 | 9/2004 | Wahlstrand et al. | |
| 2004/0176830 A1 | 9/2004 | Fang | |
| 2004/0186529 A1 | 9/2004 | Bardy et al. | |
| 2004/0204673 A1 | 10/2004 | Flaherty | |
| 2004/0210292 A1 | 10/2004 | Bardy et al. | |
| 2004/0210293 A1 | 10/2004 | Bardy et al. | |
| 2004/0210294 A1 | 10/2004 | Bardy et al. | |
| 2004/0215308 A1 | 10/2004 | Bardy et al. | |
| 2004/0220624 A1 | 11/2004 | Ritscher et al. | |
| 2004/0220626 A1 | 11/2004 | Wagner | |
| 2004/0220639 A1 | 11/2004 | Mulligan et al. | |
| 2004/0230283 A1 | 11/2004 | Prinzen et al. | |
| 2004/0249431 A1 | 12/2004 | Ransbury et al. | |
| 2004/0260348 A1 | 12/2004 | Bakken et al. | |
| 2004/0267303 A1 | 12/2004 | Guenst | |
| 2005/0061320 A1 | 3/2005 | Lee et al. | |
| 2005/0070962 A1 | 3/2005 | Echt et al. | |
| 2005/0102003 A1 | 5/2005 | Grabek et al. | |
| 2005/0149138 A1 | 7/2005 | Min et al. | |
| 2005/0159781 A1 | 7/2005 | Hsu | |
| 2005/0165466 A1 | 7/2005 | Morris et al. | |
| 2005/0182465 A1 | 8/2005 | Ness | |
| 2005/0203410 A1 | 9/2005 | Jenkins | |
| 2005/0283208 A1 | 12/2005 | Von Arx et al. | |
| 2005/0288743 A1 | 12/2005 | Min et al. | |
| 2006/0025822 A1 | 2/2006 | Zhang | |
| 2006/0042830 A1 | 3/2006 | Maghribi et al. | |
| 2006/0052829 A1 | 3/2006 | Sun et al. | |
| 2006/0052830 A1 | 3/2006 | Spinelli et al. | |
| 2006/0064135 A1 | 3/2006 | Brockway | |
| 2006/0064149 A1 | 3/2006 | Belacazar et al. | |
| 2006/0085039 A1 | 4/2006 | Hastings et al. | |
| 2006/0085041 A1 | 4/2006 | Hastings et al. | |
| 2006/0085042 A1 | 4/2006 | Hastings et al. | |
| 2006/0095078 A1 | 5/2006 | Tronnes | |
| 2006/0106442 A1 | 5/2006 | Richardson et al. | |
| 2006/0116746 A1 | 6/2006 | Chin | |
| 2006/0135999 A1 | 6/2006 | Bodner et al. | |
| 2006/0136004 A1 | 6/2006 | Cowan et al. | |
| 2006/0161061 A1 | 7/2006 | Echt et al. | |
| 2006/0200002 A1 | 9/2006 | Guenst | |
| 2006/0206151 A1 | 9/2006 | Lu | |
| 2006/0212079 A1 | 9/2006 | Routh et al. | |
| 2006/0241701 A1 | 10/2006 | Markowitz et al. | |
| 2006/0241705 A1 | 10/2006 | Neumann et al. | |
| 2006/0247672 A1 | 11/2006 | Vidlund et al. | |
| 2006/0259088 A1 | 11/2006 | Pastore et al. | |
| 2006/0265018 A1 | 11/2006 | Smith et al. | |
| 2007/0004979 A1 | 1/2007 | Wojciechowicz et al. | |
| 2007/0016098 A1 | 1/2007 | Kim et al. | |
| 2007/0027508 A1 | 2/2007 | Cowan | |
| 2007/0078490 A1 | 4/2007 | Cowan et al. | |
| 2007/0088394 A1 | 4/2007 | Jacobson | |
| 2007/0088396 A1 | 4/2007 | Jacobson | |
| 2007/0088397 A1 | 4/2007 | Jacobson | |
| 2007/0088398 A1 | 4/2007 | Jacobson | |
| 2007/0088405 A1 | 4/2007 | Jacobson | |
| 2007/0135882 A1 | 6/2007 | Drasler et al. | |
| 2007/0135883 A1 | 6/2007 | Drasler et al. | |
| 2007/0150037 A1 | 6/2007 | Hastings et al. | |
| 2007/0150038 A1 | 6/2007 | Hastings et al. | |
| 2007/0156190 A1 | 7/2007 | Cinbis | |
| 2007/0219525 A1 | 9/2007 | Gelfand et al. | |

(56) References Cited

U.S. PATENT DOCUMENTS

| | | |
|---|---|---|
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299480 A1 | 12/2007 | Hill |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0138058 A1 | 5/2009 | Cooke et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M. |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0248115 A1* | 10/2009 | Corndorf ............ A61N 1/37252 607/60 |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299438 A1 | 12/2009 | Nolan et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1* | 1/2010 | Wu ................... H04W 52/0245 607/30 |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0069983 A1 | 3/2010 | Peacock, III et al. |
| 2010/0094367 A1 | 4/2010 | Sen |
| 2010/0106222 A1* | 4/2010 | Lychou ............. A61N 1/37276 607/60 |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160557 A1* | 6/2011 | Cinbis ................. A61B 5/0028 600/374 |
| 2011/0160558 A1 | 6/2011 | Rassatt et al. |
| 2011/0160565 A1 | 6/2011 | Stubbs et al. |
| 2011/0160801 A1* | 6/2011 | Markowitz .......... A61B 5/0031 607/60 |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0270341 A1 | 11/2011 | Ruben et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0016305 A1 | 1/2012 | Jollota et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0245665 A1 | 9/2012 | Friedman et al. |

(56) References Cited

U.S. PATENT DOCUMENTS

| | | |
|---|---|---|
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0289776 A1 | 11/2012 | Keast et al. |
| 2012/0289815 A1 | 11/2012 | Keast et al. |
| 2012/0290021 A1 | 11/2012 | Saurkar et al. |
| 2012/0290025 A1 | 11/2012 | Keimel |
| 2012/0296381 A1 | 11/2012 | Matos |
| 2012/0303078 A1 | 11/2012 | Li et al. |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0027186 A1* | 1/2013 | Cinbis ............... A61B 5/0028 340/10.1 |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0192611 A1 | 8/2013 | Taepke, II et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253309 A1 | 9/2013 | Allan et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100624 A1 | 4/2014 | Ellingson |
| 2014/0100627 A1 | 4/2014 | Min |
| 2014/0107723 A1 | 4/2014 | Hou et al. |
| 2014/0112408 A1* | 4/2014 | Ecker ............... H04W 52/0229 375/271 |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222015 A1 | 8/2014 | Keast et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0330326 A1 | 11/2014 | Thompson-Nauman et al. |
| 2014/0337922 A1 | 11/2014 | Sievert et al. |
| 2014/0343348 A1 | 11/2014 | Kaplan et al. |
| 2014/0371818 A1 | 12/2014 | Bond et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045868 A1 | 2/2015 | Bonner et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0126854 A1 | 5/2015 | Keast et al. |
| 2015/0157861 A1 | 6/2015 | Aghassian |
| 2015/0157866 A1 | 6/2015 | Demmer et al. |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |

(56) References Cited

U.S. PATENT DOCUMENTS

| | | |
|---|---|---|
| 2015/0221898 A1 | 8/2015 | Chi et al. |
| 2015/0224315 A1 | 8/2015 | Stahmann |
| 2015/0224320 A1 | 8/2015 | Stahmann |
| 2015/0230699 A1 | 8/2015 | Berul et al. |
| 2015/0238769 A1 | 8/2015 | Demmer et al. |
| 2015/0258345 A1 | 9/2015 | Smith et al. |
| 2015/0290467 A1 | 10/2015 | Ludwig |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306401 A1 | 10/2015 | Demmer et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335884 A1 | 11/2015 | Khairkhahan et al. |
| 2015/0360041 A1 | 12/2015 | Stahmann et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0051823 A1* | 2/2016 | Maile ............ A61B 5/1102 607/16 |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0228701 A1 | 8/2016 | Huelskamp et al. |
| 2016/0317825 A1 | 11/2016 | Jacobson |
| 2016/0322907 A1* | 11/2016 | Hwang ............ H02M 1/4266 |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0049325 A1 | 2/2017 | Schmidt et al. |
| 2017/0056664 A1 | 3/2017 | Kane et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2018/0256902 A1 | 9/2018 | Toy et al. |
| 2018/0256909 A1 | 9/2018 | Smith et al. |
| 2018/0264262 A1 | 9/2018 | Haasl et al. |
| 2018/0264270 A1 | 9/2018 | Koop et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0339160 A1 | 11/2018 | Carroll |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904170 A2 | 4/2008 |
| EP | 1978866 A1 | 10/2008 |
| EP | 1904166 B1 | 6/2011 |
| EP | 2471452 A1 | 7/2012 |
| EP | 2433675 B1 | 1/2013 |
| EP | 2441491 B1 | 1/2013 |
| EP | 2452721 B1 | 11/2013 |
| EP | 2662113 A3 | 11/2013 |
| EP | 1948296 B1 | 1/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9528987 A1 | 11/1995 |
| WO | 9528988 A1 | 11/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 5/2002 |
| WO | 02098282 A2 | 12/2002 |
| WO | 2005000206 A3 | 1/2005 |
| WO | 2005042089 A1 | 5/2005 |
| WO | 200609215 A1 | 6/2006 |
| WO | 2006065394 A1 | 6/2006 |
| WO | 2006086435 A3 | 8/2006 |
| WO | 2006113659 A1 | 10/2006 |
| WO | 2006124833 A3 | 11/2006 |
| WO | 2007073435 A1 | 6/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 7/2013 |
| WO | 2013184787 A1 | 12/2013 |
| WO | 2014120769 A1 | 8/2014 |

OTHER PUBLICATIONS

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(384): 324-331, 1970.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration for Application No. PCT/US2016/016608, 2016, 11 pages, dated Apr. 21, 2016.

(PCT/US2016/013139) PCT Notification of Transmittal of the International Search Report and the Written Opinion of the International Searching Authority, dated Apr. 14, 2016, 12 pages.

(PCT/US2017/029540) PCT Notification of Transmittal of the International Search Report and the Written Opinion of the International Searching Authority, dated Jun. 28, 2017, 11 pages.

International Search Report and Written Opinion dated Jun. 28, 2017 for International Application No. PCT/US2017/029540.

International Search Report and Written Opinion dated Apr. 14, 2016 for International Application No. PCT/US2016/013139.

International Search Report and Written Opinion dated Apr. 21, 2016 for International Application No. PCT/US2016/016608.

(56) References Cited

OTHER PUBLICATIONS

International Search Report and Written Opinion for Application No. PCT/US2018/051529, 10 pages, dated Dec. 10, 2018.

\* cited by examiner

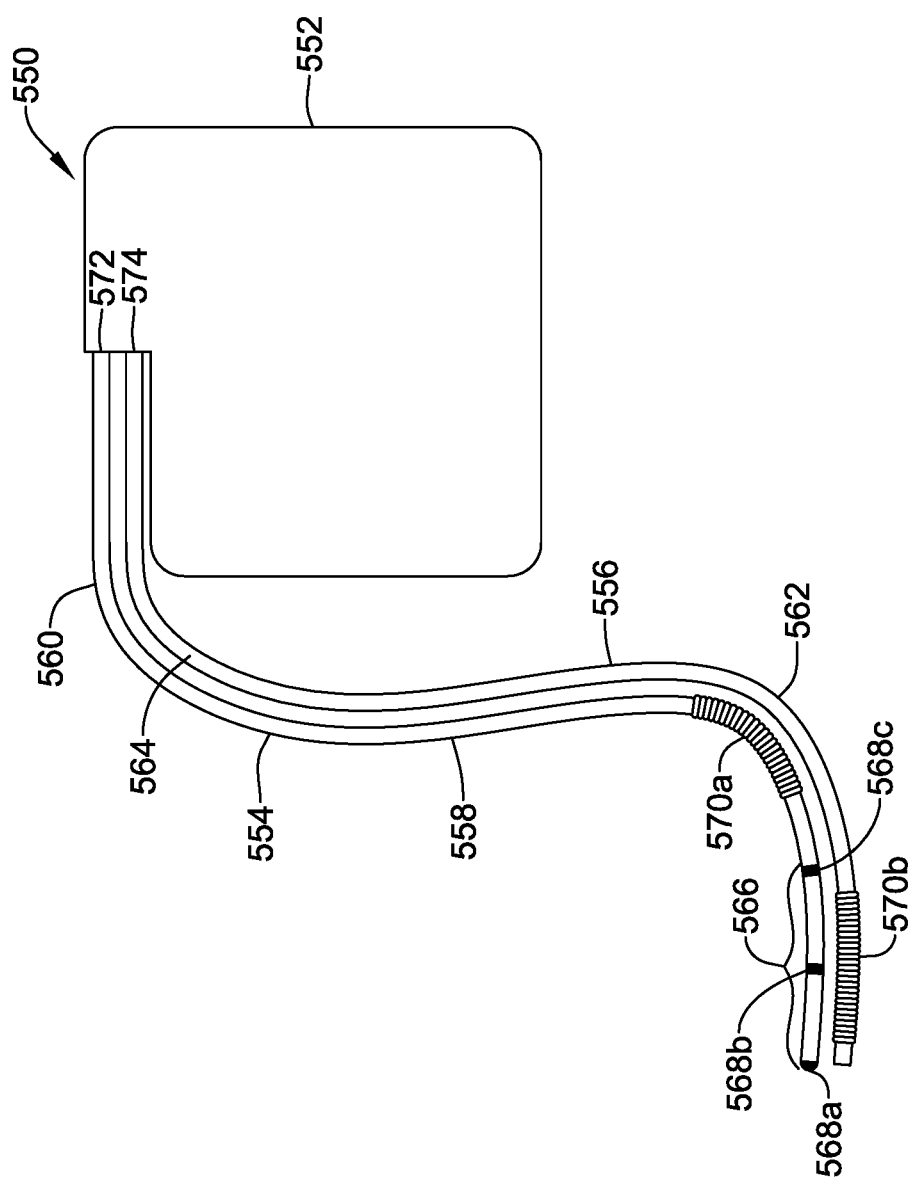

IMPLANTABLE MEDICAL DEVICE WITH MULTIPLE MODES OF OPERATION

CROSS REFERENCE TO RELATED APPLICATIONS

This application claims the benefit of U.S. Provisional Patent Application Ser. No. 62/561,052 filed on Sep. 20, 2017, the disclosure of which is incorporated herein by reference.

TECHNICAL FIELD

The disclosure relates generally to implantable medical devices, and more particularly to implantable medical devices that have multiple power modes or levels of operation or the need for power saving conditions.

BACKGROUND

Implantable medical devices are commonly used to perform a variety of functions, such as to monitor one or more conditions and/or delivery therapy to a patient. For example, an implantable medical device may deliver neurostimulation therapy to a patient. In another example, an implantable medical device may simply monitor one or more conditions, such as pressure, acceleration, cardiac events, and may communicate the detected conditions or events to another device, such as another implantable medical device or an external programmer.

In some cases, an implantable medical device may be configured to deliver pacing and/or defibrillation therapy to a patient. Such implantable medical devices may treat patients suffering from various heart conditions that may result in a reduced ability of the heart to deliver sufficient amounts of blood to a patient's body. In some cases, heart conditions may lead to rapid, irregular, and/or inefficient heart contractions. To help alleviate some of these conditions, various devices (e.g., pacemakers, defibrillators, etc.) are often implanted into a patient's body. When so provided, such devices can monitor and provide therapy, such as electrical stimulation therapy, to the patient's heart to help the heart operate in a more normal, efficient and/or safe manner. For some conditions, a patient may have multiple implanted devices that cooperate to monitor and/or provide therapy to the patient's heart.

In some cases, an Implantable Medical Device (IMD) may receive commands or other information from another IMD. However, due to the energy required to continuously maintain a communication link, the local power source of an IMD may have a shortened lifetime. What would be desirable is an IMD that can selectively place the communication link in a lower power mode when the IMD determines that the communication link is not needed, thereby potentially increasing the operational lifetime of the IMD.

SUMMARY

The disclosure relates generally to implantable medical devices, and more particularly to implantable medical devices that can operate a communication link in two or more power modes or levels. While a leadless cardiac pacemaker is used as an example implantable medical device, it should be understood that the disclosure can be applied to any suitable implantable medical device including, for example, neuro-stimulators, diagnostic devices including those that do not deliver therapy, and/or any other suitable implantable medical device as desired.

In some cases, the disclosure pertains to an implantable medical devices (IMD) such as leadless cardiac pacemakers (LCP) that may include a receiver having a higher power mode and a lower power mode. In one example, in the higher power mode, the receiver can receive a communication from an external device and pass the received communication to a controller. In the lower power mode the receiver operates at less than its maximum power level. Additionally, in some cases, the LCP may also include a physiological sensor providing an output to the controller. The controller may be configured to control whether the receiver is in the higher power mode or the lower power mode based at least in part on the output of the physiological sensor.

Alternatively or additionally to any of the embodiments above, in the lower power mode the receiver may not receive the communication from the external device and pass the received communication to the controller and the implantable medical device may be configured to operate independently of the external device when the receiver is in the lower power mode.

Alternatively or additionally to any of the embodiments above, the communication from the external device may comprise a signal and the controller may be configured to control whether the receiver is in the higher power mode or the lower power mode based at least in part on the signal.

Alternatively or additionally to any of the embodiments above, the implantable medical device may be configured to receive a command from the external device when the receiver is in the higher power mode and the controller may be further configured to control whether the receiver is in the higher power mode or the lower power mode based at least in part on the command.

Alternatively or additionally to any of the embodiments above, the controller may be configured to identify a physiological parameter value based on the output of the physiological sensor and based on one or more rules conditioned at least in part on the identified physiological parameter value, may control whether the receiver is in the higher power mode or the lower power mode and the implantable medical device may be configured to use a hysteresis function when switching from the higher power mode to the lower power mode.

Alternatively or additionally to any of the embodiments above, the identified physiological parameter value may be a heart rate value, and the one or more rules may specify that the receiver is to be placed in the higher power mode when the heart rate value is above a heart rate threshold and the receiver is to be placed in the lower power mode when the heart rate value is below the heart rate threshold or the receiver is to be placed in the lower power mode when the heart rate value is above the heart rate threshold and the receiver is to be placed in the higher power mode when the heart rate value is below the heart rate threshold.

Alternatively or additionally to any of the embodiments above, the identified physiological parameter value may be a heart rate value, and the one or more rules may specify that the receiver is to be placed in the higher power mode where the receiver is intermittently placed at a higher power level from a lower power level at a first rate when the heart rate value is above a heart rate threshold, and that the receiver is to be placed in the lower power mode where the receiver is intermittently placed at the higher power level from the lower power level at a second rate when the heart rate value is below the heart rate threshold, wherein the first rate is higher than the second rate.

Alternatively or additionally to any of the embodiments above, the identified physiological parameter value may be a heart rate value, and the one or more rules may specify that the receiver is to be placed in the higher power mode where the receiver is place at a higher power level more than at a lower power level when the heart rate value is above a heart rate threshold, and that the receiver is to be placed in the lower power mode where the receiver is placed at the lower power level more than the higher power level when the heart rate value is below the heart rate threshold.

Alternatively or additionally to any of the embodiments above, the identified physiological parameter value may be one of a heart rate value, a PH value, a potassium level, a glucose level, an ammonium level, a temperature value, a respiration rate, a ECG morphology value, an accelerometer value, a posture of a patient, a time of day.

Alternatively or additionally to any of the embodiments above, the implantable medical device may be a leadless cardiac pacemaker (LCP).

In another example of the disclosure, a leadless cardiac pacemaker (LCP) may include a housing, one or more physiological sensors for sensing one or more physiological parameters of a patient, two or more electrodes at least two of which for delivering pacing pulses to a heart of the patient, and a receiver disposed within the housing and configured to operate in a lower power mode and a higher power mode, wherein in the higher power mode, the receiver can receive an anti-tachyarrhythmia pacing (ATP) command from an external device and in the lower power mode the receiver cannot receive the ATP command from the external device. The LCP may further include operational circuitry operatively coupled to the one or more physiological sensors, the two or more electrodes, and the receiver. The operational circuitry may be configured to switch the receiver between the lower power mode and the higher power mode based at least in part on a heart rate of the patient determined based at least in part on one or more physiological parameters sensed by one or more of the physiological sensors. The operational circuitry may also deliver anti-tachyarrhythmia pacing (ATP) therapy via two or more of the electrodes in response to the receiver receiving an ATP command from the external device when the receiver is in the higher power mode.

Alternatively or additionally to any of the embodiments above, the operational circuitry may be configured to place the receiver in the higher power mode when the heart rate exceeds an ATP heart rate threshold and place the receiver in the lower power mode when the heart rate does not exceed the ATP heart rate threshold.

Alternatively or additionally to any of the embodiments above, the operational circuitry may be configured to switch the receiver to the higher power mode when the heart rate exceeds a heart rate threshold, and in the higher power mode, place the receiver at a higher power level more than a lower power level, and switch the receiver to the lower power mode when the heart rate does not exceed the heart rate threshold, and in the lower mode power, place the receiver at the lower power level more than the higher power level.

Alternatively or additionally to any of the embodiments above, the one or more physiological sensors may comprise two or more of the electrodes.

Alternatively or additionally to any of the embodiments above, the one or more physiological sensors may comprise one or more cardiac electrical sensors, and the one or more physiological parameters comprise one or more electrical signals produced by the one or more cardiac electrical sensors.

Alternatively or additionally to any of the embodiments above, the one or more physiological sensors may comprise a mechanical sensor, and the one or more physiological parameters comprise one or more mechanical signals produced by the mechanical sensor.

In another example of the disclosure, a leadless cardiac pacemaker (LCP) may be provided that includes a housing, one or more physiological sensors for sensing one or more physiological parameters of a patient, two or more electrodes for delivering pacing pulses to a heart of the patient, a receiver with an adjustable power level, and electronics operatively coupled to the one or more physiological sensors, the two or more electrodes, and the receiver. The electronics may be configured to adjust the receiver between a lower power level and a higher power level based at least in part on the one or more of the physiological parameters sensed by one or more of the physiological sensors, wherein in the higher power level the receiver can receive a command and/or other information from an external device, and in the lower power level the receiver cannot receive the command and/or other information from the external device and operate the LCP independently of the external device when the receiver is at the lower power level.

Alternatively or additionally to any of the embodiments above, the LCP may be configured to operate in cooperation with the external device, at least at times when the receiver is at the higher power level.

Alternatively or additionally to any of the embodiments above, the LCP may be configured to operate in accordance with a command received from the external device when the receiver is at the higher power level.

Alternatively or additionally to any of the embodiments above, the command may be an ATP trigger command.

BRIEF DESCRIPTION OF THE FIGURES

The disclosure may be more completely understood in consideration of the following description in connection with the accompanying drawings, in which:

FIG. 5B is a side view of an illustrative Implantable Cardiac Defibrillator (ICD) that can communicate with the LCP of FIG. 5A;

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following description should be read with reference to the drawings in which similar structures in different drawings are numbered the same. The drawings, which are not necessarily to scale, depict illustrative embodiments and are not intended to limit the scope of the disclosure.

Figure 1:
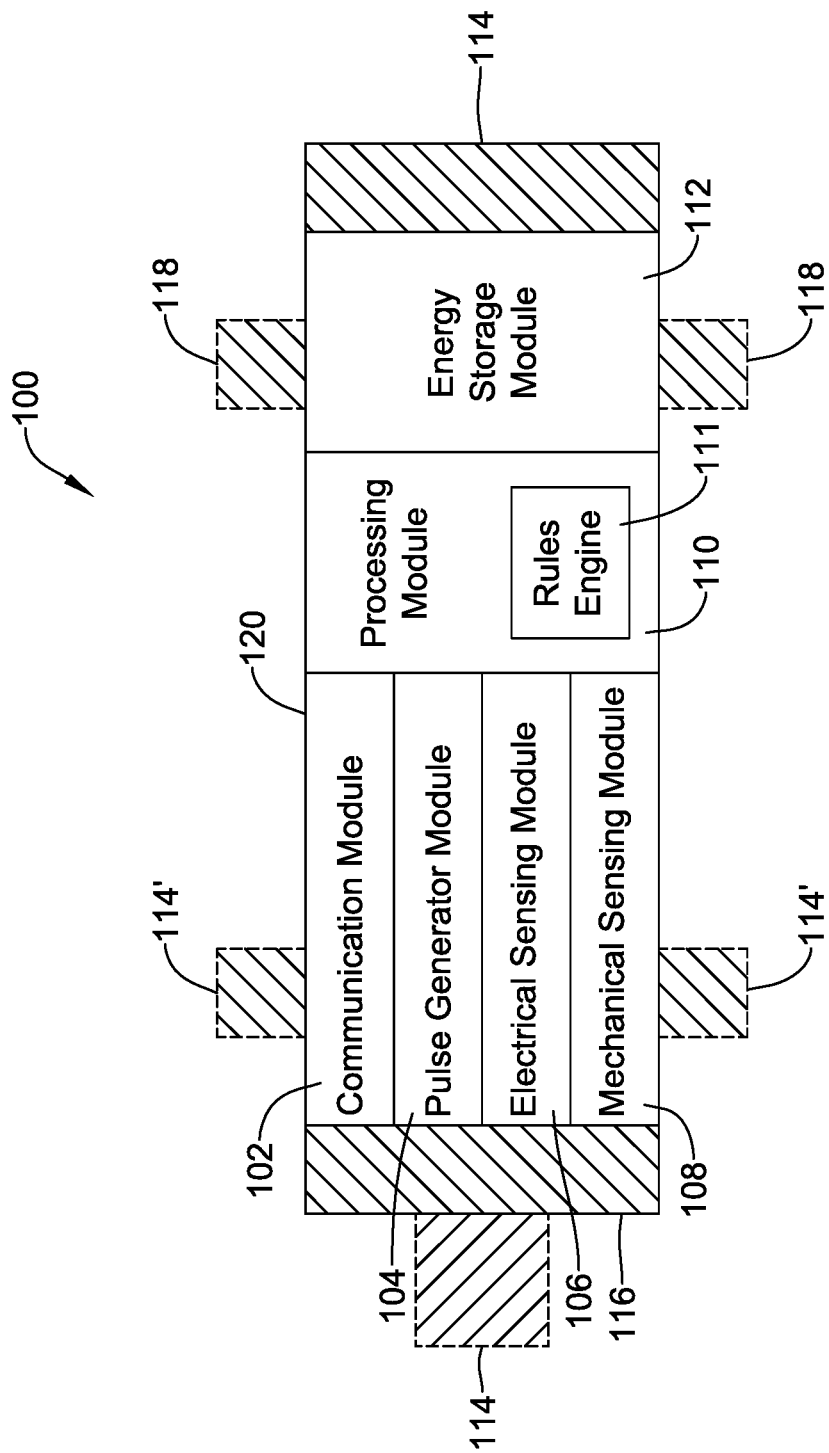
FIG. 1 is a schematic block diagram of an illustrative LCP in accordance with an example of the disclosure.

FIG. 1 depicts an illustrative cardiac pacemaker (e.g., a Leadless Cardiac Pacemaker (LCP) 100) that may be implanted into a patient and may operate to deliver appropriate therapy to the heart, such as to deliver demand pacing therapy (e.g. for bradycardia), anti-tachycardia pacing (ATP) therapy, post-shock pacing therapy, cardiac resynchronization therapy (CRT) and/or the like. While an LCP is used as an example implantable cardiac pacemaker, it should be recognized that the disclosure may be applied to any suitable implantable medical device (IMD) including, for example, neuro-stimulators, diagnostic devices including those that do not deliver therapy, and/or any other suitable implantable medical device as desired.

As can be seen in FIG. 1, the illustrative LCP 100 may be a compact device with all components housed within the or directly on a housing 120. As stated above, in some cases, the LCP 100 may be considered as being an example of an IMD. In the example shown in FIG. 1, the LCP 100 may optionally include an electrode arrangement 114, a physiological sensor arrangement 118, an energy storage module 112, a processing module, an electrical sensing module 106, a mechanical sensing module 108, a pulse generator module 104 and a communications module 102. The communications module 102 may include a receiver and/or a transmitter, and may have different power modes or power levels. In some cases, the processing module 110 may include a rules engine 111 that can execute one or more rules. In some cases, the one or more rules can specify when the receiver of the communications module 102 is in a lower power mode or a higher power mode, as further detailed below. In some cases, the one or more rules can specify how much transmittal power may be generated for a pacing pulse, an amplitude of a pacing pulse, and/or a width of a pacing pulse. In some instances, the rules engine 111 may be configured with other rules that may dictate the operation of the LCP 100 and enhance the longevity of the LCP 100. It is contemplated that the LCP 100 may include more or less modules than those shown in FIG. 1, depending on the application.

The electrical sensing module 106 may be configured to sense one or more physiological parameters of a patient. In some examples, the physiological parameters may include the cardiac electrical activity of the heart. For example, the electrical sensing module 106 may be connected to sensors 118 and the electrical sensing module 106 may be configured to sense the physiological parameters of the patient via the sensors 118. In some examples, the electrical sensing module 106 may be connected to electrodes 114/114', and the electrical sensing module 106 may be configured to sense one or more of the physiological parameters of the patient, including cardiac electrical signals, via the electrodes 114/114'. In this case, the electrodes 114/114' are the sensors.

In some examples, the mechanical sensing module 108, when provided, may be configured to sense one or more physiological parameters of the patient. For example, in certain embodiments, the mechanical sensing module 108 may include one or more sensors, such as an accelerometer, a pressure sensor, a heart sound sensor, a blood-oxygen sensor, a chemical sensor (e.g. PH), a temperature sensor, a flow sensor and/or any other suitable sensor that is configured to detect one or more mechanical/chemical physiological parameters of the patient (e.g., heart motion, heart sound, etc.). The mechanical sensing module 108 may receive and measure the physiological parameters. Both the electrical sensing module 106 and the mechanical sensing module 108 may be connected to the processing module 110, which may provide signals representative of the sensed parameters. Although described with respect to FIG. 1 as separate sensing modules, in some cases, the electrical sensing module 106 and the mechanical sensing module 108 may be combined into a single sensing module, as desired.

According to various embodiments, the physiological parameters may be indicative of the state of the patient and/or the state of the heart of the patient. For example, in some cases, the physiological parameters may include PH level, potassium level, glucose level, ammonium level, pielectrocardiogram (ECG) morphology, temperature (e.g., blood temperature, body tissue temperature, etc.), cardiac electrical signals, etc. In addition, in some examples, the cardiac electrical signals may represent local information from the chamber in which the LCP 100 is implanted. For instance, if the LCP 100 is implanted within a ventricle of the heart (e.g. RV, LV), cardiac electrical signals sensed by the LCP 100 through the electrodes 114/114' and/or sensors 118 may represent ventricular cardiac electrical signals. In some cases, the LCP 100 may be configured to detect cardiac electrical signals from other chambers (e.g. far field), such as the P-wave from the atrium.

The electrodes 114/114' can be secured relative to the housing 120 and may be exposed to the tissue and/or blood surrounding the LCP 100. In some cases, depending on the sensor type, the sensors 118 may be internal to the housing or exposed to the tissue and/or blood surrounding the LCP 100. In some cases, the electrodes 114 may be generally disposed on either end of the LCP 100. In some examples, the electrodes 114/114' and sensors 118 may be in electrical communication with one or more of the modules 102, 104, 106, 108, and 110. The electrodes 114/114' and/or sensors 118 may be supported by the housing 120. In some examples, the electrodes 114/114' and/or sensors 118 may be connected to the housing 120 through short connecting wires such that the electrodes 114/114' and/or sensors 118 are not directly secured relative to the housing 120 but rather located on a tail that is connected the housing. In examples where the LCP 100 includes one or more electrodes 114', the electrodes 114' may in some cases be disposed on the sides of the LCP 100, which may increase the number of electrodes by which the LCP 100 may sense physiological parameters, deliver electrical stimulation, and/or communicate with an external medical device. The electrodes 114/114' and/or sensors 118 can be made up of one or more biocompatible conductive materials such as various metals or alloys that are known to be safe for implantation within a human body. In some instances, the electrodes 114/114' and/or sensors 118 connected to the LCP 100 may have an insulative portion that electrically isolates the electrodes 114/114' and/or sensors 118 from adjacent electrodes/sensors, the housing 120, and/or other parts of the LCP 100.

The processing module 110 may include electronics that is configured to control the operation of the LCP 100. For example, the processing module 110 may be configured to receive electrical signals from the electrical sensing module 106 and/or the mechanical sensing module 108. Based on the received signals, the processing module 110 may identify or determine, for example, a physiological parameter value such as a heart rate of the patient, abnormalities in the operation of the heart, etc. Based on the determined conditions, the processing module 110 may control the pulse generator module 104 to generate and deliver pacing pulses in accordance with one or more therapies to treat the determined conditions. The processing module 110 may further receive communications and/or information from the receiver of the communication module 102. In some examples, the processing module 110 may use such received communications (e.g. a command such as an ATP command, a sensed parameter or determined condition, and/or other information) to help determine the current conditions of the patient, determine whether an abnormality is occurring given the current condition, and/or to take a particular action in response to the communications. The processing module 110 may additionally control the communication module 102 to send/receive information to/from other devices.

In some examples, the processing module 110 may include a pre-programmed chip, such as a very-large-scale integration (VLSI) chip and/or an application specific integrated circuit (ASIC). In such embodiments, the chip may be pre-programmed with control logic in order to control the operation of the LCP 100. In some cases, the pre-programmed chip may implement a state machine that performs the desired functions. By using a pre-programmed chip, the processing module 110 may use less power than other programmable circuits (e.g. general purpose programmable microprocessors) while still being able to maintain basic functionality, thereby potentially increasing the battery life of the LCP 100. In other examples, the processing module 110 may include a programmable microprocessor. Such a programmable microprocessor may allow a user to modify the control logic of the LCP 100 even after implantation, thereby allowing for greater flexibility of the LCP 100 than when using a pre-programmed ASIC. In some examples, the processing module 110 may further include a memory, and the processing module 110 may store information on and read information from the memory. In other examples, the LCP 100 may include a separate memory (not shown) that is in communication with the processing module 110, such that the processing module 110 may read and write information to and from the separate memory.

The energy storage module 112 may provide power to the LCP 100 for its operations. Because the LCP 100 is an implantable device, access to the LCP 100 may be limited after implantation. Accordingly, it is desirable to have sufficient battery capacity to deliver therapy over a period of treatment such as days, weeks, months, years or even decades. In some instances, the energy storage module 112 may be a rechargeable battery, which may help increase the useable lifespan of the LCP 100. In other examples, the energy storage module 112 may be some other type of power source, as desired. In some cases, the energy storage module 112 may be a primary (non-rechargeable) battery (e.g., $FeS_2$). In some cases, the energy storage module 112 may not be battery at all, but rather may be super capacitor or other charge storage device. In still other examples, the energy storage module 112 may be some other type of power source, such as a fuel cell, nuclear battery, or the like, as desired.

In the example shown in FIG. 1, the pulse generator module 104 may be electrically connected to the electrodes 114/114'. In some cases, the sensors 118 may also have electrical stimulation functionality and may be electrically connected to the pulse generator module 104 when desired. Said another way, one or more of the electrodes 114/114' may function as a sensor 118 electrode, such as for sensing cardiac electrical signals. In some cases, the LCP 100 may have a controllable switch that connects one or more of the electrodes 114/114' to the pulse generator module 104 when the pulse generator module 104 delivers a pacing pulse, and may connect one or more of the electrodes 114/114' to the electrical sensing module 106 when the pulse generator module 104 is not delivering a pacing pulse.

The pulse generator module 104 may be configured to generate electrical stimulation signals. For example, the pulse generator module 104 may generate and deliver electrical pacing pulses by using energy stored in the energy storage module 112 within the LCP 100 and deliver the generated pacing pulses via the electrodes 114, 114' and/or sensors 118. Alternatively, or additionally, the pulse generator 104 may include one or more capacitors, and the pulse generator 104 may charge the one or more capacitors by drawing energy from the energy storage module 112. The pulse generator 104 may then use the energy of the one or more capacitors to deliver the generated pacing pulses via the electrodes 114, 114', and/or sensors 118. In at least some examples, the pulse generator 104 of the LCP 100 may include switching circuitry to selectively connect one or more of the electrodes 114, 114' and/or sensors 118 to the pulse generator 104 in order to select which of the electrodes 114/114' and/or sensors 118 (and/or other electrodes) the pulse generator 104 uses to deliver the electrical stimulation therapy. The pulse generator module 104 may be configured to deliver pacing pulses at two or more different energy levels. This may be accomplished by controlling the amplitude, pulse width, pulse shape and/or any other suitable characteristic of the pacing pulses.

According to various embodiments, the sensors 118 may be configured to sense one or more physiological parameters of a patient and send a signal to the electrical sensing module 106 and/or the mechanical sensing module 108. For example, the physiological parameters may include a cardiac electrical signal and the sensors 118 may send a response signal to the electrical sensing module 106. In some examples, one or more of the sensors 118 may be an accelerometer and the physiological parameters may alternatively or additionally include heart motion and/or heart sounds and the sensors 118 may send a corresponding signal to the mechanical sensing module 108. Based on the sensed signals, the sensing modules 106 and/or 108 may determine or measure one or more physiological parameters, such as heart rate, PH level, potassium level, glucose level, ammonium level, temperature (e.g., blood temperature, body tissue temperature, etc.), ECG morphology, respiration rate, time of day, posture of the patient, activity level of the patient and/or any other suitable physiological parameter(s). The one or more physiological parameters may then be passed to the processing module 110.

In certain embodiments, communication module 102 may be configured to communicate with other devices such as remote sensors, other medical devices such as neuro-stimulators, diagnostic devices including those that do not deliver therapy, and/or any other suitable implantable medical device located externally to the LCP 100. Such devices may be located either external or internal to the patient's body. Irrespective of the location, external devices (i.e. external to the LCP 100 but not necessarily external to the patient's body) can communicate with the LCP 100 via communication module 102 to accomplish one or more desired functions. For example, the LCP 100 may communicate information, such as sensed electrical signals, data, instructions, messages, R-wave detection markers, etc., to an external medical device (e.g. SICD and/or programmer) through the communication module 102. The external medical device may use the communicated signals, data, instructions, messages, R-wave detection markers, etc., to perform various functions, such as determining occurrences of arrhythmias, delivering electrical stimulation therapy, storing received data, and/or performing any other suitable function. The LCP 100 may additionally receive information such as signals, data, commands or instructions and/or messages from the external medical device through the receiver of the communication module 102, and the LCP 100 may use the received signals, data, commands or instructions and/or messages to perform various functions, such as determining occurrences of arrhythmias, delivering electrical stimulation therapy, storing received data, and/or performing any other suitable function. The communication module 102 may be configured to use one or more methods for communicating with external devices. For example, the communication module 102 may communicate via radiofrequency (RF) signals, inductive coupling, optical signals, acoustic signals, conducted communication signals, and/or any other signals suitable for communication. According to various embodiments, at least the receiver of the communication module 102 may be configured to operate in two or more modes or two or more power levels. In some cases, the receiver of the communication module 102 may be capable of receiving communication from the external device and passing the received communication to the processing module 110 (e.g. controller) in a first power mode or level, and incapable of receiving communication from the external device and passing the received communication to the processing module 110 (e.g. controller) in a second power mode or level. In some cases, the receiver of the communication module 102 may initially be in a lower power mode or level and changes into a higher power mode level when a valid communication signal or command is received. In some cases, the receiver may have a dynamic hysteresis or lag when alternating from a first power mode (e.g., a higher power mode) to a second mode (e.g., lower power mode). Furthermore, in certain embodiments, the processing module 110 may use sensed physiological parameters, such as heart rate, PH level, potassium level, glucose level, ammonium level, temperature (e.g., blood temperature, body tissue temperature, etc.), ECG morphology, respiration rate, time of day, posture of the patient, activity level of the patient and/or any other suitable physiological parameter(s) sensed or determined by the electrical sensing module 106 and/or mechanical sensing module 108 to set the power mode of the communication module 102. In some cases, the processing module 110 includes a rules engine 111 that can execute one or more predetermined rules. In some cases, the one or more predetermined rules can specify when the receiver of the communications module 102 is set to a lower power mode or a higher power mode. For example, in some cases, a predetermined rule may specify that the receiver of the communication module 102 is to be set to a lower power mode when the sensed intrinsic heart rate of the patient is at or below a heart rate threshold, and that the receiver of the communication module 102 is to be set to a higher power mode when the sensed intrinsic heart rate of the patient is above the heart rate threshold. In some cases, the processing module 110 may receive physiological parameters from the electrical sensing module 106 and/or mechanical sensing module 108 (or other module) and identify the intrinsic heart rate of the patient. The rules engine 111 of the processing module 110 may then determine if the intrinsic heart rate is below or above the heart rate threshold. When the intrinsic heart rate is at or below the heart rate threshold, the rules engine 111 may set the receiver of the communication module 102 to a lower power mode, where the communication module 102 is incapable of receiving communication from an external device or passing a received communication to the processing module 110 (e.g. controller). Likewise, when the intrinsic heart rate is above the heart rate threshold, the rules engine 111 may set the receiver of the communication module 102 to a higher power mode, where the communication module 102 is capable of receiving communication from an external device and passing a received communication to the processing module 110 (e.g. controller). In some cases, in the lower power mode, the receiver of the communication module 102 may consume between 0% and 90% of its maximum power level, between 5% and 75% of its maximum power level, below 80% of the maximum power level, below 60% of the maximum power level, below 50% of the maximum power level, below 30% of the maximum power level, below 20% of the maximum power level, below 10% of the maximum power level, or any other suitable level. The heart rate threshold may be a fixed heart rate such as a rate limit, or may be a dynamic heart rate that is dependent on, for example, the activity level of the patient. In this configuration, the energy used to power the LCP 100 (e.g., power from the energy storage module 112) may be conserved and potentially extend the operating life of the LCP 100. In some cases, the intrinsic heart rate may rise above the heart rate threshold. In this case, the intrinsic heart rate observed may be a fast but regular rhythm, such as that observed during ventricular tachycardia. In response to the intrinsic heart rate reaching and/or exceeding the heart rate threshold, the processing module 110 may be configured to place the receiver of the communication module 102 in the higher power mode such that the receiver of the communication module 102 may be capable of communicating with an external device. In some embodiments, the receiver of the communication module 102 may operate at its maximum power level when in the higher power mode. In this case, if or when the receiver of the communication module 102 receives communication signals from an external device, the receiver of the communication module 102 may be configured to pass the received communication to the processing module 110. In some cases, the communication may include a command from the external device commanding the LCP 100 to deliver ATP therapy, post-shock pacing therapy, cardiac resynchronization therapy (CRT), etc. or other suitable therapy. In response to receiving the command (e.g., an ATP trigger command), the processing module 110 may execute the received command (e.g. delivery ATP therapy). When the intrinsic heart rate is below the heart rate threshold, the processing module 110 may be configured to place the receiver of the communication module 102 in the lower power mode such that the receiver of the communication module 102 ignores any communication from the external device. In some cases, the processing module 110 may have a dynamic hysteresis or lag configured to wait a period of time before placing the receiver of the communication module 102 back in the lower power mode. For example, when the intrinsic heart rate goes from above the heart rate threshold to below the heart rate threshold, the processing module 110 may wait 5 seconds before placing the receiver back into the lower power mode. In some cases, this may allow enough time to determine that the patient's heart rate is going to remain below the heart rate threshold. In other examples, the dynamic hysteresis or lag may be 10 seconds, 30 seconds, 1 minute, 5 minutes, 10 minutes, 30 minutes, 1 hour, 5 hours, 10 hours, 24 hours, etc. In some cases, the processing module 110 may be configured to identify if the intrinsic heart rate of the patient is above a therapy threshold, which may be the same or different from the heart rate threshold discussed above. When different (e.g., the therapy threshold is larger than the heart rate threshold used for communication), the processing module 110 may receive an ATP command from the external device when the intrinsic heart rate is above the heart rate threshold, but may wait to verify that the intrinsic heart rate is above the therapy threshold before actually delivering ATP therapy to the patient via the pulse generator module 104.

In another example, in some cases, a predetermined rule may specify that the receiver of the communication module 102 is to be set to a lower power mode until communication is received from an external device. In the lower power mode, the communication module 102 may be capable of receiving communication from an external device, however, the receiver may consume between 0% and 90% of its maximum power level, between 5% and 75% of its maximum power level, below 80% of the maximum power level, below 60% of the maximum power level, below 50% of the maximum power level, below 30% of the maximum power level, below 20% of the maximum power level, below 10% of the maximum power level, or any other suitable level. When communication is received, the rules engine 111 of the processing module 110 may then determine if the communication is a valid telemetry command from the external device. If the rule engine 111 determines that the communication is valid, the processing module 110 may be configured to place the receiver of the communication module 102 in the higher power mode. In some embodiments, the receiver of the communication module 102 may operate at its maximum power level when in the higher power mode. In this case, when in the higher power mode, the receiver of the communication module 102 may be configured to pass the telemetry command to the processing module 110. In some cases, the telemetry command may be a command to deliver ATP therapy, post-shock pacing therapy, cardiac resynchronization therapy (CRT), etc. or other suitable therapy. In response to receiving the command (e.g., an ATP trigger command), the processing module 110 may execute the received command (e.g. delivery ATP therapy). When the command has been executed, the processing module 110 may be configured to place the receiver of the communication module 102 back into the lower power mode. In some cases, the processing module 110 may have a dynamic hysteresis or lag configured to wait a period of time after the command has been executed before placing the receiver of the communication module 102 back in the lower power mode. For example, when the processing module 110 executes the command, the processing module 110 may wait 5 seconds before placing the receiver back into the lower power mode. In some cases, this may allow enough time to determine that the patient's heart rate is going to remain below the heart rate threshold. In other examples, the dynamic hysteresis or lag may be 10 seconds, 30 seconds, 1 minute, 5 minutes, 10 minutes, 30 minutes, 1 hour, 5 hours, 10 hours, 24 hours, etc.

In some cases, the external device may have sent the telemetry command because the external device sensed that the intrinsic heart rate of the patient is above the heart rate threshold discussed above. In some cases, once the processing module 110 has received the command, the processing module 110 may wait to verify that the intrinsic heart rate is above the therapy threshold before actually delivering ATP therapy to the patient via the pulse generator module 104. As discussed above, the therapy threshold may be the same or different from the heart rate threshold (e.g., the therapy threshold is larger than the heart rate threshold used for communication). In some cases, rather than remaining at a constant lower power level when the intrinsic heart rate of the patient is at or below the heart rate threshold, and at a constant higher power level when the intrinsic heart rate of the patient is above the heart rate threshold, it is contemplated that the lower power mode and/or the higher power mode may switch between a lower power level and a higher power level, where the lower power mode may be at the lower power level more of the time than the higher power level. For example, the receiver of the communication module 102 may switch between the lower power level and the higher power level at a duty cycle, where the duty cycle is higher (at the higher power level longer) in the higher power mode than in the lower power mode. In some cases, the receiver of the communication module 102 may switch between a higher power level and a lower power level in the lower power mode, but may remain at a higher power level when in the higher power mode. At the lower power level, the receiver of the communication module 102 may be incapable of communicating with an external device, and at the higher power level, the receiver may be capable of communicating with an external device. These are just some examples. While intrinsic heart rate is used here as an example physiological parameter, it is contemplated that any suitable physiological parameter or combination of physiological parameters may be used.

This is just one example of how the processing module 110 may adjust the receiver of the communication module 102 between the lower power mode or level and the higher power mode or level. In other embodiments, the fluctuation between the lower power mode or level and the higher power mode or level may be different. This example has been used to illustrate how the processing module 110 and the receiver of the communication module 102 may be customized to help increase the battery life and thus the useful lifetime of the LCP 100. In some cases, the rules engine 111 of the processing module 110 may be configured with one or more rules that determines how much transmittal power may be generated for a pacing pulse, an amplitude of a pacing pulse, and/or a width of a pacing pulse. In some instances, the rules engine 111 may be configured with other rules that may dictate the operation of the LCP 100 and enhance the longevity of the LCP 100.

To implant the LCP 100 inside a patient's body, an operator (e.g., a physician, clinician, etc.), may fix the LCP 100 to cardiac tissue of the patient's heart. To facilitate fixation, the LCP 100 may include one or more anchors 116. The anchors 116 may include any one of a number of fixation or anchoring mechanisms. For example, the anchor 116 may include one or more pins, staples, threads, screws, helix, tines, and/or the like. In some examples, although not shown, the anchor 116 may include threads on its external surface that may run along at least a partial length of the anchor 116. The threads may provide friction between the cardiac tissue and the anchor to help fix the anchor 116 within the cardiac tissue. In other examples, the anchor 116 may include other structures such as barbs, spikes, or the like to facilitate engagement with the surrounding cardiac tissue.

Figure 2:
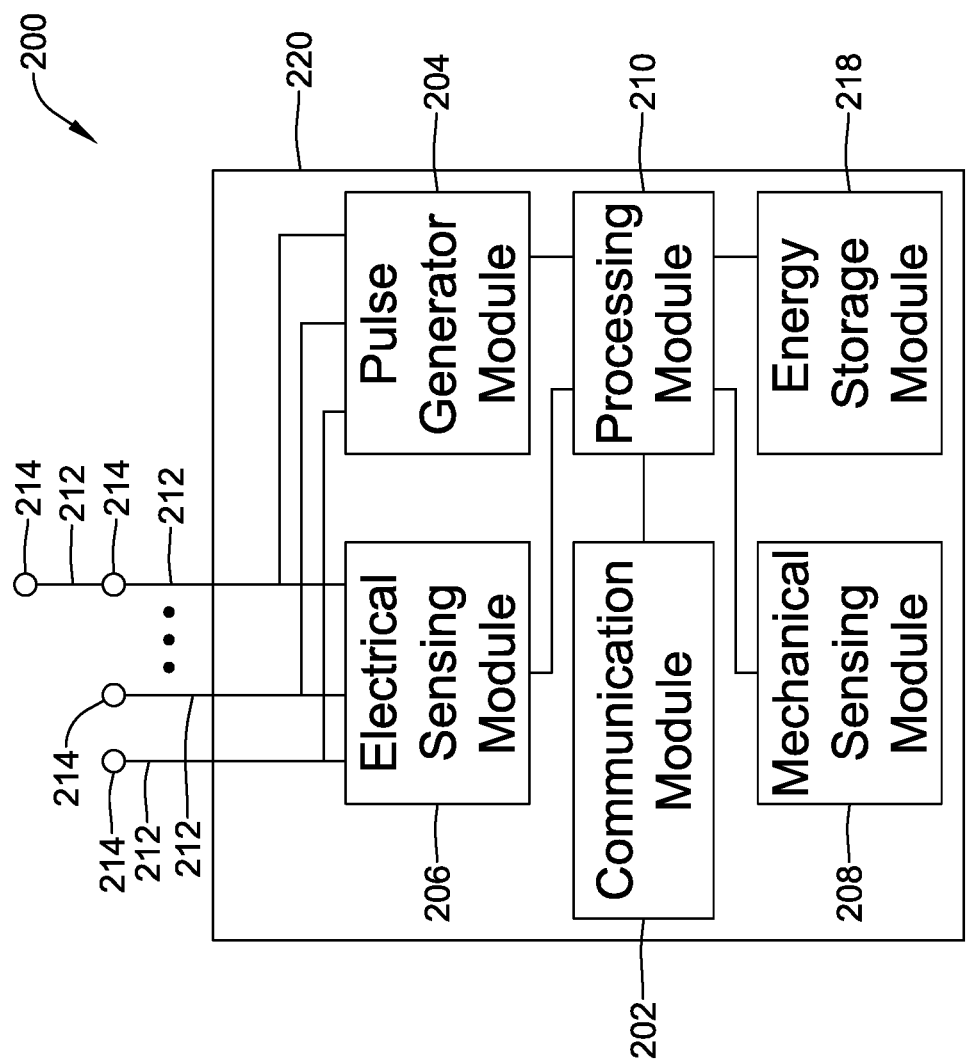
FIG. 2 is a schematic block diagram of another illustrative medical device that may be used in conjunction with the LCP of FIG. 1.

FIG. 2 depicts an example of another or second medical device (MD) 200, which may be used in conjunction with the LCP 100 (FIG. 1) in order to detect and/or treat cardiac abnormalities. In some cases, the MD 200 may be considered as an example of the IMD and/or the LCP. In the example shown, the MD 200 may include a communication module 202, a pulse generator module 204, an electrical sensing module 206, a mechanical sensing module 208, a processing module 210, and an energy storage module 218. Each of these modules may be similar to the modules 102, 104, 106, 108, and 110 of LCP 100. Additionally, the energy storage module 218 may be similar to the energy storage module 112 of the LCP 100. In some examples, however, the MD 200 may have a larger volume within the housing 220. In such examples, the MD 200 may include a larger energy storage module 218 and/or a larger processing module 210 capable of handling more complex operations than the processing module 110 of the LCP 100.

While it is contemplated that the MD 200 may be another leadless device such as shown in FIG. 1, in some instances the MD 200 may include leads such as leads 212. The leads 212 may include electrical wires that conduct electrical signals between the electrodes 214 and one or more modules located within the housing 220. In some cases, the leads 212 may be connected to and extend away from the housing 220 of the MD 200. In some examples, the leads 212 are implanted on, within, or adjacent to a heart of a patient. The leads 212 may contain one or more electrodes 214 positioned at various locations on the leads 212, and in some cases at various distances from the housing 220. Some leads 212 may only include a single electrode 214, while other leads 212 may include multiple electrodes 214. Generally, the electrodes 214 are positioned on the leads 212 such that when the leads 212 are implanted within the patient, one or more of the electrodes 214 are positioned to perform a desired function. In some cases, the one or more of the electrodes 214 may be in contact with the patient's cardiac tissue. In some cases, the one or more of the electrodes 214 may be positioned subcutaneously and/or substernum and outside of the patient's heart. In some cases, the electrodes 214 may conduct intrinsically generated electrical signals to the leads 212, e.g. signals representative of intrinsic cardiac electrical activity. The leads 212 may, in turn, conduct the received electrical signals to one or more of the modules 202, 204, 206, and 208 of the MD 200. In some cases, the MD 200 may generate electrical stimulation signals, and the leads 212 may conduct the generated electrical stimulation signals to the electrodes 214. The electrodes 214 may then conduct the electrical signals and deliver the signals to the patient's heart (either directly or indirectly).

The mechanical sensing module 208, as with the mechanical sensing module 108, may contain or be electrically connected to one or more sensors, such as accelerometers, acoustic sensors, blood pressure sensors, heart sound sensors, blood-oxygen sensors, temperature sensors, and/or other sensors which are configured to measure one or more mechanical/chemical parameters of the heart and/or patient. In some examples, one or more of the sensors may be located on the leads 212, but this is not required. In some examples, one or more of the sensors may be located in the housing 220.

While not required, in some examples, the MD 200 may be an implantable medical device. In such examples, the housing 220 of the MD 200 may be implanted in, for example, a transthoracic region of the patient. The housing 220 may generally include any of a number of known materials that are safe for implantation in a human body and may, when implanted, hermetically seal the various components of the MD 200 from fluids and tissues of the patient's body.

In some cases, the MD 200 may be an implantable cardiac pacemaker (LCP). In this example, the MD 200 may have one or more leads, for example the leads 212, which are implanted on or within the patient's heart. The one or more leads 212 may include one or more electrodes 214 that are in contact with cardiac tissue and/or blood of the patient's heart. The MD 200 may be configured to sense intrinsically generated cardiac electrical signals and determine, for example, one or more cardiac arrhythmias based on analysis of the sensed signals. The MD 200 may be configured to deliver CRT, ATP therapy, bradycardia therapy, and/or other therapy types via the leads 212 implanted within the heart. In some examples, the MD 200 may additionally be configured to provide defibrillation therapy.

In some instances, the MD 200 may be an implantable cardioverter-defibrillator (ICD). In such examples, the MD 200 may include one or more leads implanted within a patient's heart. The MD 200 may also be configured to sense cardiac electrical signals, determine occurrences of tachyarrhythmias based on the sensed signals, and may be configured to deliver defibrillation therapy in response to determining an occurrence of a tachyarrhythmia. In other examples, the MD 200 may be a subcutaneous implantable cardioverter-defibrillator (S-ICD). In examples where the MD 200 is an S-ICD, one of the leads 212 may be a subcutaneously implanted lead. In at least some examples where the MD 200 is an S-ICD, the MD 200 may include only a single lead which is implanted subcutaneously, but this is not required. In some instances, the lead(s) may have one or more electrodes that are placed subcutaneously and outside of the chest cavity. In other examples, the lead(s) may have one or more electrodes that are placed inside of the chest cavity, such as just interior of the sternum but outside of the heart.

In some example, when the MD 200 determines occurrences of tachyarrhythmias, the MD 200 may use the communication module 202 and the leads 212 to communicate such occurrences to one or more other implanted devices (e.g., the LCP 100, from FIG. 1). In one example, the one or more other implanted devices may be configured to operate in one or more power modes or levels. In this case, the other implanted devices may be capable of receiving the communications from the MD 200 in a first power mode or level (e.g., a higher and/or maximum power mode or level) and incapable of receiving the communications from the MD 200 in a second power mode or level (e.g., a lower and/or non-maximum power mode or level). In the latter case, the other implanted devices may operate relatively independently of the MD 200.

In some examples, the MD 200 may not be an implantable medical device. Rather, the MD 200 may be a device external to the patient's body, and may include skin-electrodes that are placed on a patient's body. In such examples, the MD 200 may be able to sense surface electrical signals (e.g. cardiac electrical signals that are generated by the heart or electrical signals generated by a device implanted within a patient's body and conducted through the body to the skin). In such examples, the MD 200 may be configured to deliver various types of electrical stimulation therapy, including, for example, defibrillation therapy.

Figure 3:
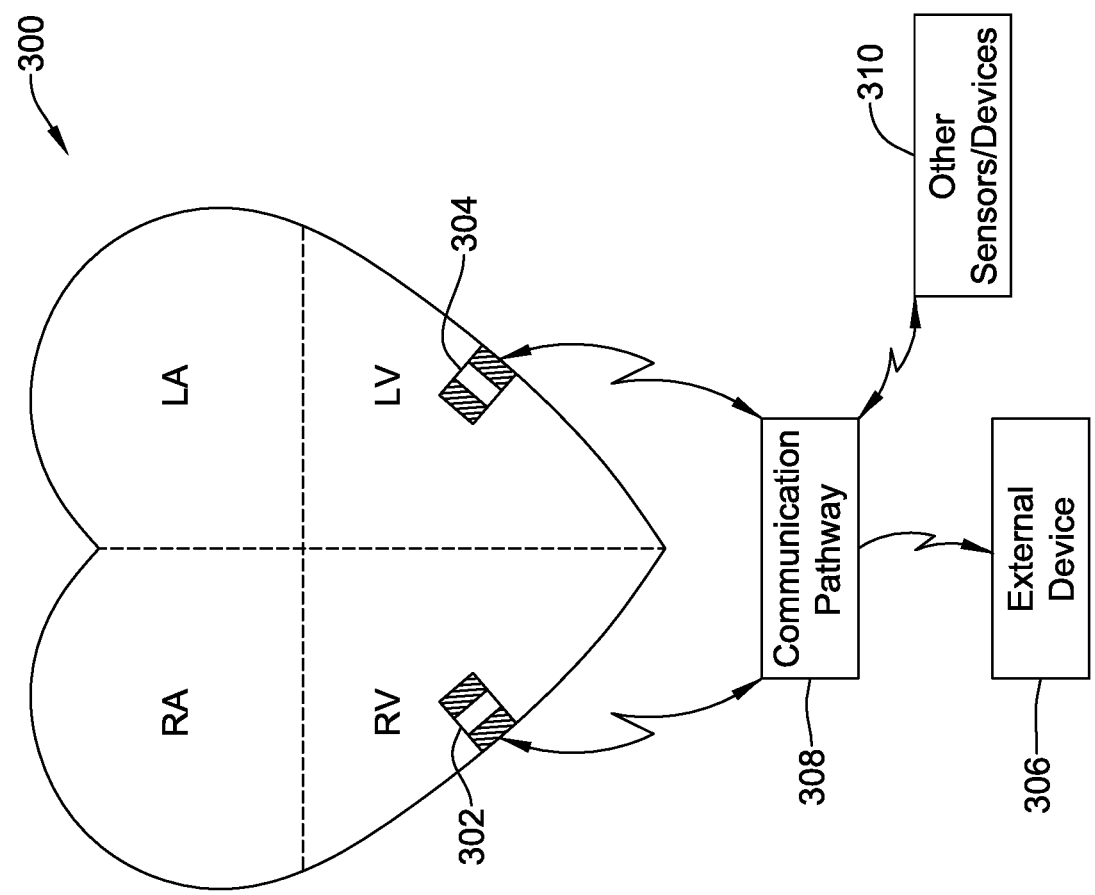
FIG. 3 is a schematic diagram of an exemplary medical system that includes multiple LCPs and/or other devices in communication with one another.

FIG. 3 illustrates an example of a medical device system and a communication pathway through which multiple medical devices 302, 304, 306, and/or 310 may communicate. In the example shown, the medical device system 300 may include LCPs 302 and 304, external medical device 306, and other sensors/devices 310. The LCPs 302 and 304 may be any of the devices described previously with respect to the LCP 100. The external device 306 may be any of the devices described previously with respect to the MD 200. Other sensors/devices 310 may also be any of the devices described previously with respect to the MD 200. In some instances, other sensors/devices 310 may include a sensor, such as an accelerometer, an acoustic sensor, a blood pressure sensor, or the like. In some cases, other sensors/devices 310 may include an external programmer device that may be used to program one or more devices of the system 300.

Various devices of the system 300 may communicate via communication pathway 308. For example, the LCPs 302 and/or 304 may sense intrinsic cardiac electrical signals and may communicate such signals to one or more other devices 302/304, 306, and 310 of the system 300 via communication pathway 308. In one example, one or more of the devices 302/304 may receive such signals and, based on the received signals, determine an occurrence of an arrhythmia. In some cases, the device or devices 302/304 may communicate such determinations to one or more other devices 306 and 310 of the system 300. In some cases, one or more of the devices 302/304, 306, and 310 of the system 300 may take action based on the communicated determination of an arrhythmia, such as by delivering a suitable electrical stimulation to the heart of the patient.

Additionally and/or alternatively, in some cases the external device 306 and/or the other sensors/devices 310 may sense intrinsic cardiac electrical signals and may communicate such signals to one or more other devices 302/304, 306, and 310 of the system 300 via communication pathway 308. In one example, one or more of the devices 306/310 may receive such signals and based on the received signals, determine an occurrence of an arrhythmia. In some cases, the device or devices 306/310 may communicate such determinations to the LCPs 302 and 304 of the system 300.

In some cases, as described above in regard to LCP 100, the LCPs 302 and 304 may be configured to operate in two or more modes or two or more power levels. In some cases, the LCPs 302 and 304 may be capable of receiving communications or commands (e.g., an ATP trigger command) from the device or devices 306/310 via the communication pathway 308 in a first power mode or level (e.g., a higher and/or maximum power mode or level) and incapable of receiving communications or commands (e.g., an ATP trigger command) from the device or devices 306/310 in a second power mode or level (e.g., a lower and/or non-maximum power mode or level). In the latter case, the LCPs 302 and 304 may operate relatively independently of the device or devices 306/310. Furthermore, in certain embodiments, the LCPs 302 and 304 may use sensed physiological parameters, such as PH levels, potassium levels, glucose levels, ammonium levels, electrocardiogram (ECG) morphology, temperature (e.g., blood temperature, body tissue temperature, etc.), cardiac electrical signals, etc., to place the LCPs 302 and 304 in a power mode or level based upon one or more rules. For example, the heart rate value of a patient may be identified from the sensed physiological parameters and the one or more rules may specify that the LCP 302 and/or 304 may be placed in a higher power mode or level when the heart rate value is above a heart rate threshold and the LCP 302 and/or 304 may be placed in a lower power mode or level when the heart rate value is below the heart rate threshold. In another example, the heart rate value of the patient may be identified from the sensed physiological parameters and the one or more rules may specify that when the heart rate value is above the heart rate threshold, the LCP 302 and/or 304 may be intermittently placed in the higher power mode or level from the lower power mode or level more frequently over a period of time than when the heart rate value is below the heart rate threshold. In another example, the heart rate value of the patient may be identified from the sensed physiological parameters and the one or more rules may specify that when the heart rate value is above the heart rate threshold, the LCP 302 and/or 304 may be placed in the higher power mode or level for a longer period of time than the lower power mode. In addition, the one or more rules may specify that when the heart rate value is below the heart rate threshold, the LCP 302 and/or 304 may be placed in the lower power mode or level for a longer period of time than the higher power mode.

It is contemplated that the communication pathway 308 may communicate using RF signals, inductive coupling, optical signals, acoustic signals, or any other signals suitable for communication. Additionally, in at least some examples, communication pathway 308 may include multiple signal types. For instance, other sensors/device 310 may communicate with the external device 306 using a first signal type (e.g. RF communication) but communicate with the LCPs 302/304 using a second signal type (e.g. conducted communication). Further, in some examples, communication between devices may be limited. For instance, as described above, in some examples, the LCPs 302/304 may communicate with the external device 306 only through other sensors/devices 310, where the LCPs 302/304 send signals to other sensors/devices 310, and other sensors/devices 310 relay the received signals to the external device 306.

In some cases, the communication pathway 308 may include conducted communication. Accordingly, devices of the system 300 may have components that allow for such conducted communication. For instance, the devices of system 300 may be configured to transmit conducted communication signals (e.g. current and/or voltage pulses) into the patient's body via one or more electrodes of a transmitting device, and may receive the conducted communication signals (e.g. pulses) via one or more electrodes of a receiving device. The patient's body may "conduct" the conducted communication signals (e.g. pulses) from the one or more electrodes of the transmitting device to the electrodes of the receiving device in the system 300. In such examples, the delivered conducted communication signals (e.g. pulses) may differ from pacing or other therapy signals. For example, the devices of the system 300 may deliver electrical communication pulses at an amplitude/pulse width that is sub-capture threshold to the heart. Although, in some cases, the amplitude/pulse width of the delivered electrical communication pulses may be above the capture threshold of the heart, but may be delivered during a blanking period of the heart (e.g. refractory period) and/or may be incorporated in or modulated onto a pacing pulse, if desired.

Delivered electrical communication pulses may be modulated in any suitable manner to encode communicated information. In some cases, the communication pulses may be pulse width modulated or amplitude modulated. Alternatively, or in addition, the time between pulses may be modulated to encode desired information. In some cases, conducted communication pulses may be voltage pulses, current pulses, biphasic voltage pulses, biphasic current pulses, or any other suitable electrical pulse as desired. Alternatively, or in addition, the communication pathway 308 may include radiofrequency (RF) communication, inductive communication, optical communication, acoustic communication and/or any other suitable communication, as desired.

Figure 4:
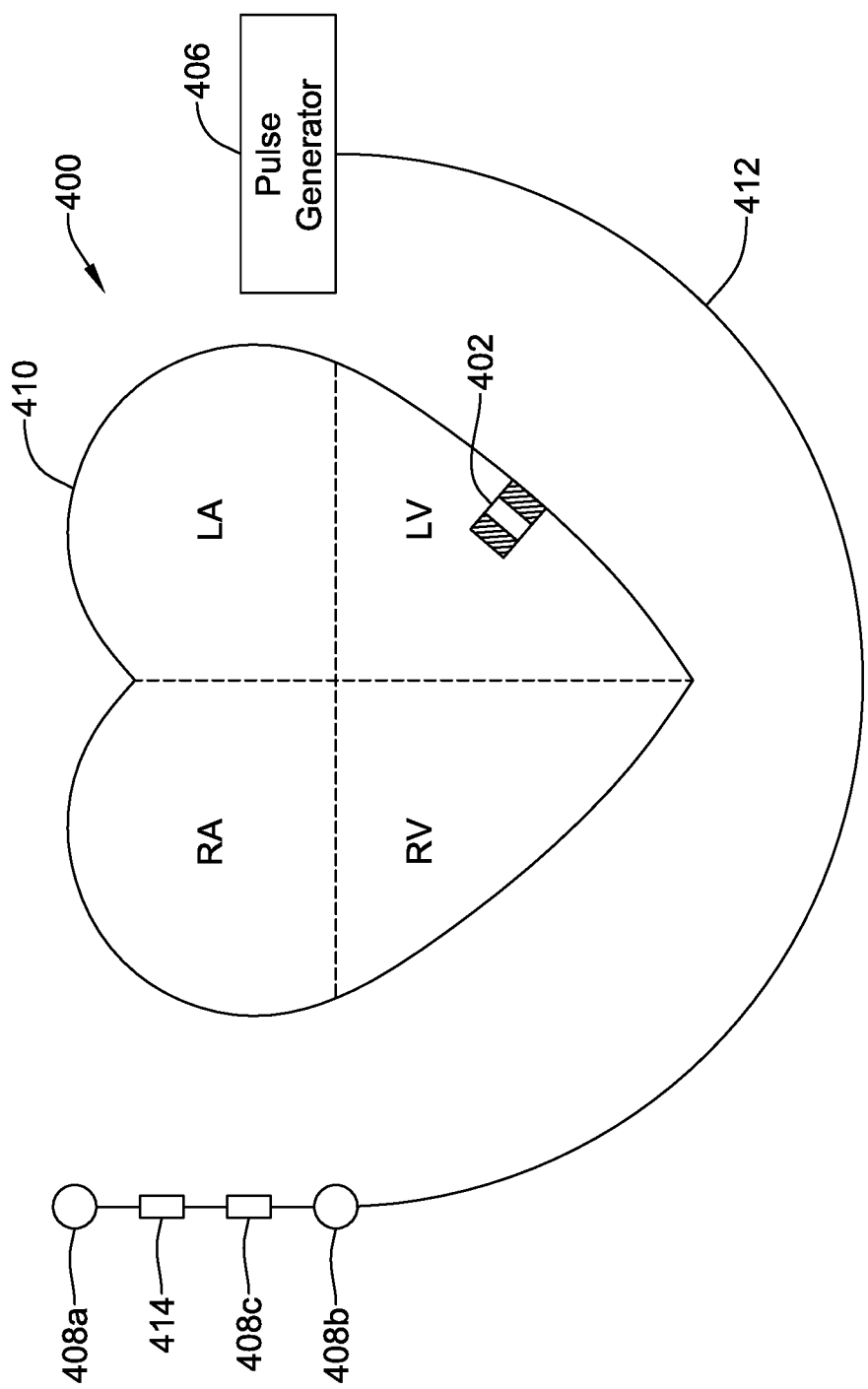
FIG. 4 is a schematic diagram of another illustrative system that includes an LCP and another medical device.

FIG. 4 shows an illustrative medical device system. In FIG. 4, an LCP 402 is shown fixed to the interior of the left ventricle of the heart 410, and a pulse generator 406 is shown coupled to a lead 412 having one or more electrodes 408a-408c. In some cases, the pulse generator 406 may be part of a subcutaneous implantable cardioverter-defibrillator (S-ICD), and the one or more electrodes 408a-408c may be positioned subcutaneously. In some cases, the one or more electrodes 408a-408c may be placed inside of the chest cavity but outside of the heart, such as just interior of the sternum.

In some cases, the LCP 402 may communicate with the subcutaneous implantable cardioverter-defibrillator (S-ICD). In some cases, the lead 412 and/or pulse generator 406 may include an accelerometer 414 that may, for example, be configured to sense vibrations that may be indicative of heart sounds.

In some cases, the LCP 402 may be in the right ventricle, right atrium, left ventricle or left atrium of the heart, as desired. In some cases, more than one LCP 402 may be implanted. For example, one LCP may be implanted in the right ventricle and another may be implanted in the right atrium. In another example, one LCP may be implanted in the right ventricle and another may be implanted in the left ventricle. In yet another example, one LCP may be implanted in each of the chambers of the heart.

Figure 5A:
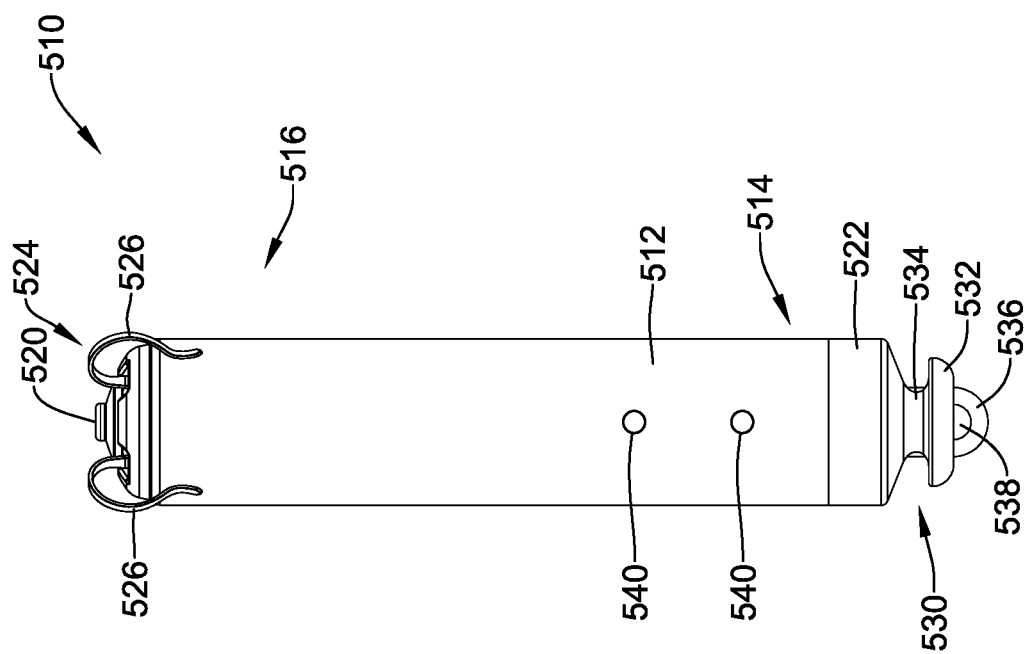
FIG. 5A is a side view of an illustrative implantable LCP.

FIG. 5A is a side view of an illustrative implantable leadless cardiac pacemaker (LCP) 510. The LCP 510 may be similar in form and function to the LCP 100 described above. The LCP 510 may include any of the modules and/or structural features described above with respect to the LCP 100 described above. The LCP 510 may include a shell or housing 512 having a proximal end 514 and a distal end 516. The illustrative LCP 510 includes a first electrode 520 secured relative to the housing 512 and positioned adjacent to the distal end 516 of the housing 512 and a second electrode 522 secured relative to the housing 512 and positioned adjacent to the proximal end 514 of the housing 512. In some cases, the housing 512 may include a conductive material and may be insulated along a portion of its length. A section along the proximal end 514 may be free of insulation so as to define the second electrode 522. The electrodes 520, 522 may be sensing and/or pacing electrodes to provide electro-therapy and/or sensing capabilities. The first electrode 520 may be capable of being positioned against or may otherwise contact the cardiac tissue of the heart while the second electrode 522 may be spaced away from the first electrode 520. The first and/or second electrodes 520, 522 may be exposed to the environment outside the housing 512 (e.g. to blood and/or tissue).

In some cases, the LCP 510 may include a pulse generator (e.g., electrical circuitry) and a power source (e.g., a battery) within the housing 512 to provide electrical signals to the electrodes 520, 522 to control the pacing/sensing electrodes 520, 522. While not explicitly shown, the LCP 510 may also include, a receiver, an electrical sensing module, a mechanical sensing module, and/or a processing module, and the associated circuitry, similar in form and function to the modules 102, 106, 108, 110 described above. The various modules and electrical circuitry may be disposed within the housing 512. Electrical connections between the pulse generator and the electrodes 520, 522 may allow electrical stimulation to heart tissue and/or sense a physiological condition.

In some cases, the receiver may operate in two or more modes or two or more power levels. In some cases, the receiver may be capable of receiving communications and/or commands from another device (e.g., MD 200, from FIG. 2) in a first power mode or level (e.g., a higher and/or maximum power mode or level) and incapable of receiving communications and/or commands from another device in a second power mode or level (e.g., a lower and/or non-maximum power mode or level). In the latter case, the LCP 510 may operate relatively independently. In this configuration, the energy used to power the LCP 510 (e.g., power from the power source) may be conserved and potentially extend the operating life of the LCP 510. Furthermore, in certain embodiments, the LCP 510 may use the electrodes 520, 522 to sense physiological parameters to place the receiver in a power mode or level based upon one or more rules that depend on one or more of the sense physiological parameters. For example, the intrinsic heart rate value of a patient may be identified from the sensed physiological parameters and one or more rules may specify that the receiver is to be placed in a higher power mode or level when the heart rate value is above a heart rate threshold and the receiver is to be placed in a lower power mode or level when the heart rate value is below the heart rate threshold. In another example, the heart rate value of the patient may be identified from the sensed physiological parameters and one or more rules may specify that when the heart rate value is above the heart rate threshold, the receiver is to be intermittently placed in the higher power mode or level from the lower power mode or level more frequently over a period of time than when the heart rate value is below the heart rate threshold. In another example, the heart rate value of the patient may be identified from the sensed physiological parameters and one or more rules may specify that when the heart rate value is above the heart rate threshold, the receiver is to be placed in the higher power mode or level for a longer period of time than the lower power mode. In addition, the one or more rules may specify that when the heart rate value is below the heart rate threshold, the receiver is to be placed in the lower power mode or level for a longer period of time than the higher power mode. While intrinsic heart rate is used here as an example physiological parameter, it is contemplated that any suitable physiological parameter or combination of physiological parameters may be used by one or more rules to control the power mode of the receiver.

In the example shown, the LCP 510 includes a fixation mechanism 524 proximate the distal end 516 of the housing 512. The fixation mechanism 524 is configured to attach the LCP 510 to a wall of the heart, or otherwise anchor the LCP 510 to the anatomy of the patient. In some instances, the fixation mechanism 524 may include one or more, or a plurality of hooks or tines 526 anchored into the cardiac tissue of the heart to attach the LCP 510 to a tissue wall. In other instances, the fixation mechanism 524 may include one or more, or a plurality of passive tines, configured to entangle with trabeculae within the chamber of the heart and/or a helical fixation anchor configured to be screwed into a tissue wall to anchor the LCP 510 to the heart. These are just examples.

The LCP 510 may further include a docking member 530 proximate the proximal end 514 of the housing 512. The docking member 530 may be configured to facilitate delivery and/or retrieval of the LCP 510. For example, the docking member 530 may extend from the proximal end 514 of the housing 512 along a longitudinal axis of the housing 512. The docking member 530 may include a head portion 532 and a neck portion 534 extending between the housing 512 and the head portion 532. The head portion 532 may be an enlarged portion relative to the neck portion 534. For example, the head portion 532 may have a radial dimension from the longitudinal axis of the LCP 510 that is greater than a radial dimension of the neck portion 534 from the longitudinal axis of the LCP 510. In some cases, the docking member 530 may further include a tether retention structure 536 extending from or recessed within the head portion 532. The tether retention structure 536 may define an opening 538 configured to receive a tether or other anchoring mechanism therethrough. While the retention structure 536 is shown as having a generally "U-shaped" configuration, the retention structure 536 may take any shape that provides an enclosed perimeter surrounding the opening 538 such that a tether may be securably and releasably passed (e.g. looped) through the opening 538. In some cases, the retention structure 536 may extend though the head portion 532, along the neck portion 534, and to or into the proximal end 514 of the housing 512. The docking member 530 may be configured to facilitate delivery of the LCP 510 to the intracardiac site and/or retrieval of the LCP 510 from the intracardiac site. While this describes one example docking member 530, it is contemplated that the docking member 530, when provided, can have any suitable configuration.

In some cases, the LCP 510 may include one or more pressure sensors 540 coupled to or formed within the housing 512 such that the pressure sensor(s) is exposed to the environment outside the housing 512 to measure blood pressure within the heart. For example, if the LCP 510 is placed in the left ventricle, the pressure sensor(s) 540 may measure the pressure within the left ventricle. If the LCP 510 is placed in another portion of the heart (such as one of the atriums or the right ventricle), the pressures sensor(s) may measure the pressure within that portion of the heart. The pressure sensor(s) 540 may include a MEMS device, such as a MEMS device with a pressure diaphragm and piezoresistors on the diaphragm, a piezoelectric sensor, a capacitor-Micro-machined Ultrasonic Transducer (cMUT), a condenser, a micro-monometer, or any other suitable sensor adapted for measuring cardiac pressure. The pressures sensor(s) 540 may be part of a mechanical sensing module described herein. It is contemplated that the pressure measurements obtained from the pressures sensor(s) 540 may be used to generate a pressure curve over cardiac cycles. The pressure readings may be taken in combination with impedance measurements (e.g. the impedance between electrodes 520 and 522) to generate a pressure-impedance loop for one or more cardiac cycles as will be described in more detail below. The impedance may be a surrogate for chamber volume, and thus the pressure-impedance loop may be representative for a pressure-volume loop for the heart.

In some embodiments, the LCP 510 may be configured to measure impedance between the electrodes 520, 522. More generally, the impedance may be measured between other electrode pairs, such as the additional electrodes 114' described above. In some cases, the impedance may be measure between two spaced LCP's, such as two LCP's implanted within the same chamber (e.g. LV) of the heart, or two LCP's implanted in different chambers of the heart (e.g. RV and LV). The processing module of the LCP 510 and/or external support devices may derive a measure of cardiac volume from intracardiac impedance measurements made between the electrodes 520, 522 (or other electrodes). Primarily due to the difference in the resistivity of blood and the resistivity of the cardiac tissue of the heart, the impedance measurement may vary during a cardiac cycle as the volume of blood (and thus the volume of the chamber) surrounding the LCP changes. In some cases, the measure of cardiac volume may be a relative measure, rather than an actual measure. In some cases, the intracardiac impedance may be correlated to an actual measure of cardiac volume via a calibration process, sometimes performed during implantation of the LCP(s). During the calibration process, the actual cardiac volume may be determined using fluoroscopy or the like, and the measured impedance may be correlated to the actual cardiac volume.

In some cases, the LCP 510 may be provided with energy delivery circuitry operatively coupled to the first electrode 520 and the second electrode 522 for causing a current to flow between the first electrode 520 and the second electrode 522 in order to determine the impedance between the two electrodes 520, 522 (or other electrode pair). It is contemplated that the energy delivery circuitry may also be configured to deliver pacing pulses via the first and/or second electrodes 520, 522. The LCP 510 may further include detection circuitry operatively coupled to the first electrode 520 and the second electrode 522 for detecting an electrical signal received between the first electrode 520 and the second electrode 522. In some instances, the detection circuitry may be configured to detect cardiac signals received between the first electrode 520 and the second electrode 522.

When the energy delivery circuitry delivers a current between the first electrode 520 and the second electrode 522, the detection circuitry may measure a resulting voltage between the first electrode 520 and the second electrode 522 (or between a third and fourth electrode separate from the first electrode 520 and the second electrode 522, not shown) to determine the impedance. When the energy delivery circuitry delivers a voltage between the first electrode 520 and the second electrode 522, the detection circuitry may measure a resulting current between the first electrode 520 and the second electrode 522 (or between a third and fourth electrode separate from the first electrode 520 and the second electrode 522) to determine the impedance.

FIG. 5B is a side view of an illustrative implantable cardiac device (ICD) 550. In various embodiments, the ICD 550 may be an example of the MD 200 described above, configured to deliver output therapy in the form of at least one of bradycardia pacing, anti-tachycardia pacing, cardiac resynchronization therapy, or defibrillation. In such examples, the ICD 550 may include a housing 552 having operational circuitry disposed within. Additionally, one or more leads 554 and 556, similar to leads 212 described above, may be connected to the operational circuitry and extend away from the housing 552.

In certain embodiments, the lead 554 may include sensing electrodes 566 at a distal end 558 adapted for sensing one or more physiological parameters. In some cases, the sensing electrodes 566 may include tip electrode 568A, electrode 568B spaced proximally away from the electrode 568A, and electrode 568C spaced proximally away from the electrodes 568A and 568B. In some examples, the lead 554 may also include a defibrillation coil 570A and the sensing electrodes 566 may be spaced distally away from the defibrillation coil 570A. In various embodiments, the ICD 550 may also include the lead 556. In some examples, the lead 556 may also include a defibrillation coil 570B at a distal end 562. As illustrated in FIG. 5B, the electrodes 570A, 570B are coil electrodes. However, other types of electrodes, for example, plural interconnected ring electrodes, may also be employed. In some examples, the lead 554 may have a proximal end 560 that includes a proximal connector 572 configured to attach the lead 554 to the housing 552 and couple the electrodes 568A-568C and 570A to the internal circuitry (i.e., the operational circuitry) of the ICD 550. Furthermore, the lead 556 may have a proximal end 564 that includes a proximal connector 574 configured to attach the lead 556 to the housing 552 and couple the electrode 570B to the operational circuitry of the ICD 550. In certain embodiments, the leads 554, 556 may also include a hollow interior extending from the proximal ends 560, 564 to the distal ends 558, 562. The hollow interior may allow for the introduction of a stylet (not shown) during implant, which may allow the leads 554, 556 to be guided through a point of venous insertion to an implant site.

The ICD 550 may be adapted for use in a cardiac therapy system. The housing 552 of the ICD 550 may be hermetically sealed. The operational circuitry within the housing 552 may include various elements such as a battery, and one or more of low-power and high-power circuitry. Low-power circuitry may be used for sensing cardiac signals including filtering, amplifying and digitizing sensed data. Low-power circuitry may also be used for certain cardiac therapy outputs such as pacing output, as well as an annunciator, such as a beeper or buzzer, telemetry circuitry for RF, conducted or inductive communication (or, alternatively, infrared, sonic and/or cellular) for use with a non-implanted programmer or communicator. The operational circuitry may also comprise memory and logic circuitry that will typically couple with one another via a control module which may include a controller or processor. High power circuitry such as high power capacitors, a charger, and an output circuit such as an H-bridge having high power switches may also be provided for delivering, for example, defibrillation therapy. Other circuitry and actuators may be included such as an accelerometer or thermistor to detect changes in patient position or temperature for various purposes, output actuators for delivering a therapeutic substance such as a drug, insulin or insulin replacement, for example.

As used herein, the coil electrodes 570A, 570B may be helically wound elements, filaments, or strands. The filament forming the coils 570A, 570B may have a generally round or a generally flat (e.g. rectangular) cross-sectional shape, as desired. However, other cross-sectional shapes may be used. The coil electrodes 570A, 570B may have a closed pitch, or in other words, adjacent windings may contact one another. Alternatively, the coil electrodes 570A, 570B may have an open pitch such that adjacent windings are spaced a distance from one another. The pitch may be uniform or varied along a length of the coil electrodes 570A, 570B. A varied pitch may be gradual tapered changes in pitch or abrupt or step-wise changes in pitch.

In some cases, the coil electrodes 570A, 570B may have a length that is generally larger than a width. Round, oval or flattened coil electrodes 570A, 570B may be used. In some cases, the coil electrodes 570A, 570B may have a length in the range of one to ten centimeters. In an example, the coil electrodes 570A, 570B may have a six or eight centimeter length. In another example, the leads 554, 556 may have two four centimeter electrode coils 570A, 570B. In some cases, the electrode coils 570A, 570B and the leads 554, 556 may be in the range of four to ten French, or larger or smaller, in outer profile. Rather than a coil electrode, a cylindrical electrode may be used having a continuous surface.

In some cases, the electrode coils 570A, 570B and leads 554, 556 may be coated. For example, a thin permeable membrane may be positioned over a shock coil or other electrode and/or other portions of the leads 554, 556 to inhibit or to promote tissue ingrowth. Coatings, such as, but not limited to expanded polytetrafluoroethylene (ePTFE) may also be applied to the coil and/or lead to facilitate extraction and/or to reduce tissue ingrowth. In some embodiments, one or more of the electrodes, whether coils, rings, or segmented electrodes, include a high capacitive coating such as, but not limited to iridium oxide (IrOx), titanium nitride (TiN), or other "fractal" coatings which may be used, for example, to improve electrical performance. Steroidal and antimicrobial coatings may be provided as well.

The various components of the devices/systems disclosed herein may include a metal, metal alloy, polymer, a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers for use in the leads discussed above may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like.

In at least some embodiments, portions or all of the accessory devices and their related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the accessory devices and their related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the accessory devices and their related components to achieve the same result.

Figure 6:
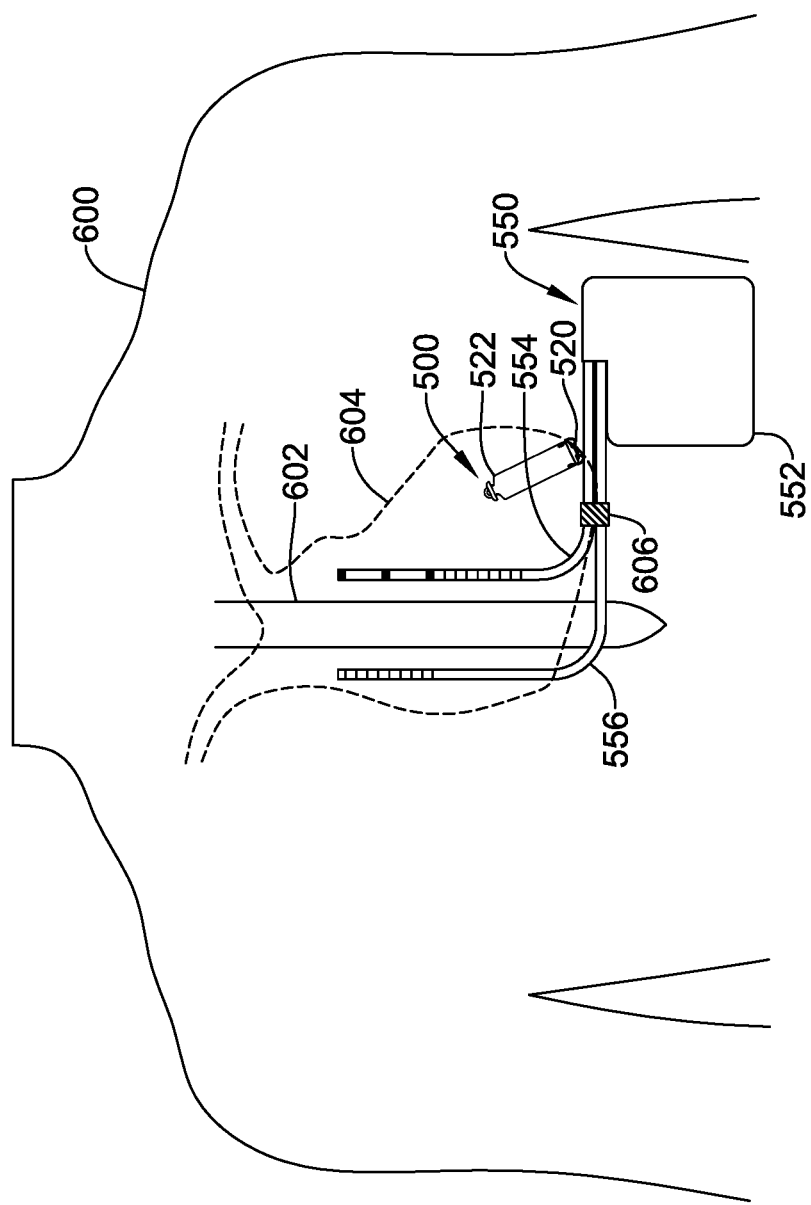
FIG. 6 is an example of the LCP of FIG. 5A and the ICD of FIG. 5B implanted within a patient.

FIG. 6 depicts an illustrative placement of the LCP 500 and the ICD 550 in a patient 600, for whom certain anatomical features are outlined including a sternum 602 and a heart 604. In some examples, the LCP 500 may be located in the right ventricle (RV) of the heart 604. In other examples, the LCP 500 may be located in another chamber of the heart 604, such as the left ventricle (LV). The ICD 550 has been placed including the leads 554, 556 and the housing 552, with the housing 552 placed at approximately the left axilla. In the illustration, a suture sleeve is shown at 606 and is used to fixate the leads 554, 556, for example, to the subcutaneous fascia of the patient 600. The housing 552 may be placed as desired, for example at the anterior axillary line, the midaxillary line, in the posterior axillary line, or may even be more dorsal with placement dorsally between the anterior surface of the serratus and the posterior surface of the latissimus dorsi. In some cases, a right sided axillary, pectoral or subclavicular left or right position may be used instead.

According to various embodiments, the receiver of the LCP 500 may be configured to operate in two or more modes or two or more power levels. In some cases, the LCP 500 may be capable of communicating with the ICD 550 in a first power mode or level and incapable of communicating with the ICD 550 in a second power mode or level. In certain embodiments, the LCP 500 may use the physiological parameters sensed by the electrodes 520 and/or 522 (and/or other electrodes and/or sensors) to place the LCP 500 in a power mode or level based upon one or more rules. For example, in some cases, a rule may specify that the receiver of the LCP 500 is to operate in a lower power mode or level if the intrinsic heart rate of the heart 604 is at or below a heart rate threshold, and the receiver of the LCP 500 is to operate in a higher power mode or level if the intrinsic heart rate of the heart 604 is above the heart rate threshold. Alternatively or additionally, in some cases, a rule may specify that the LCP 500 is to be intermittently placed at a higher power level from a lower power level at a first rate when the heart rate value is above the heart rate threshold and is to be intermittently placed at the higher power level from the lower power mode at a second rate when the heart rate value is at or below the heart rate value. In some cases, the one or more rules can specify how much transmittal power may be generated for a pacing pulse, an amplitude of a pacing pulse, and/or a width of a pacing pulse. In some instances, the LCP 500 may be configured with other rules that may dictate the operation of the LCP 500 and enhance the longevity of the LCP 500.

Figure 7:
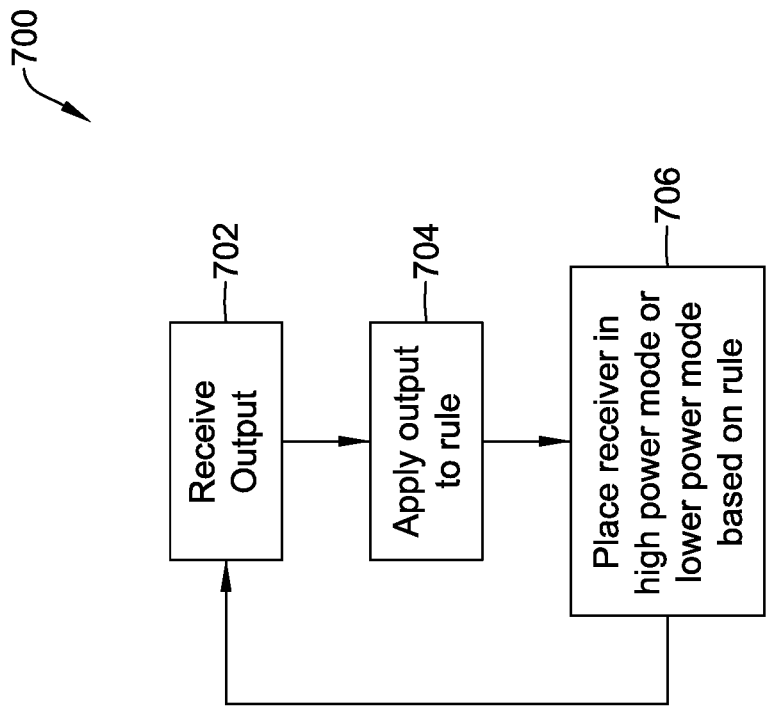
FIG. 7 is a flow diagram of an illustrative method that may be implemented by a medical device or medical device system, such as the illustrative medical devices and/or medical device systems shown in FIGS. 1-6.

FIG. 7 shows an example method 700 of operation of an IMD configured to operate at two or more power modes. Method 700 begins at step 702, where the IMD receives an output signal. In some examples, the output signal may be representative of one or more physiological parameters that are indicative of the state of the patient and/or the state of the heart of the patient. For example, in some cases, the output signals may represent physiological parameters such as PH levels, electrocardiogram (ECG) morphology, heart rate, chamber pressure, acceleration, rotation, temperature (e.g., blood temperature, body tissue temperature, etc.), cardiac electrical signals, etc. In some examples, the cardiac electrical signals may represent local information from the chamber in which the IMD may be implanted. In some cases, the IMD may be configured to detect cardiac electrical signals from other chambers (e.g. far field), such as the P-wave from the atrium. At step 704, the IMD may apply the output signal to a rule. In some cases, the output signal may be applied to one rule. In some cases, the output signal may be applied to many rules and the rules may have a hierarchy of importance where the result of a rule or rules may be ignored based upon the result of another rule or rules.

At step 706, a receiver of the IMD may be placed in a certain power mode based on the application of the rule to the output signal(s). For example, if a sensed or determined physiological parameter(s) is within an acceptable range and/or below a threshold, the receiver may be placed in the lower power mode, and if the physiological parameter(s) is outside the acceptable range and/or above the threshold, the receiver may be placed in the higher power mode. The IMD may then return to step 702.

FIGS. 8A-10 are timing diagrams showing illustrative operation of an IMD (e.g. LCP). FIGS. 8A-10 depict traces for an output signal 800 indicative of a physiological parameter, a physiological parameter threshold 802, a first lower power level 804, a second higher power level 806. According to various embodiments, an LCP may monitor the output signal 800 and may place the receiver in a lower power mode or a higher power mode based upon the application of one or more rules.

Figure 8A:
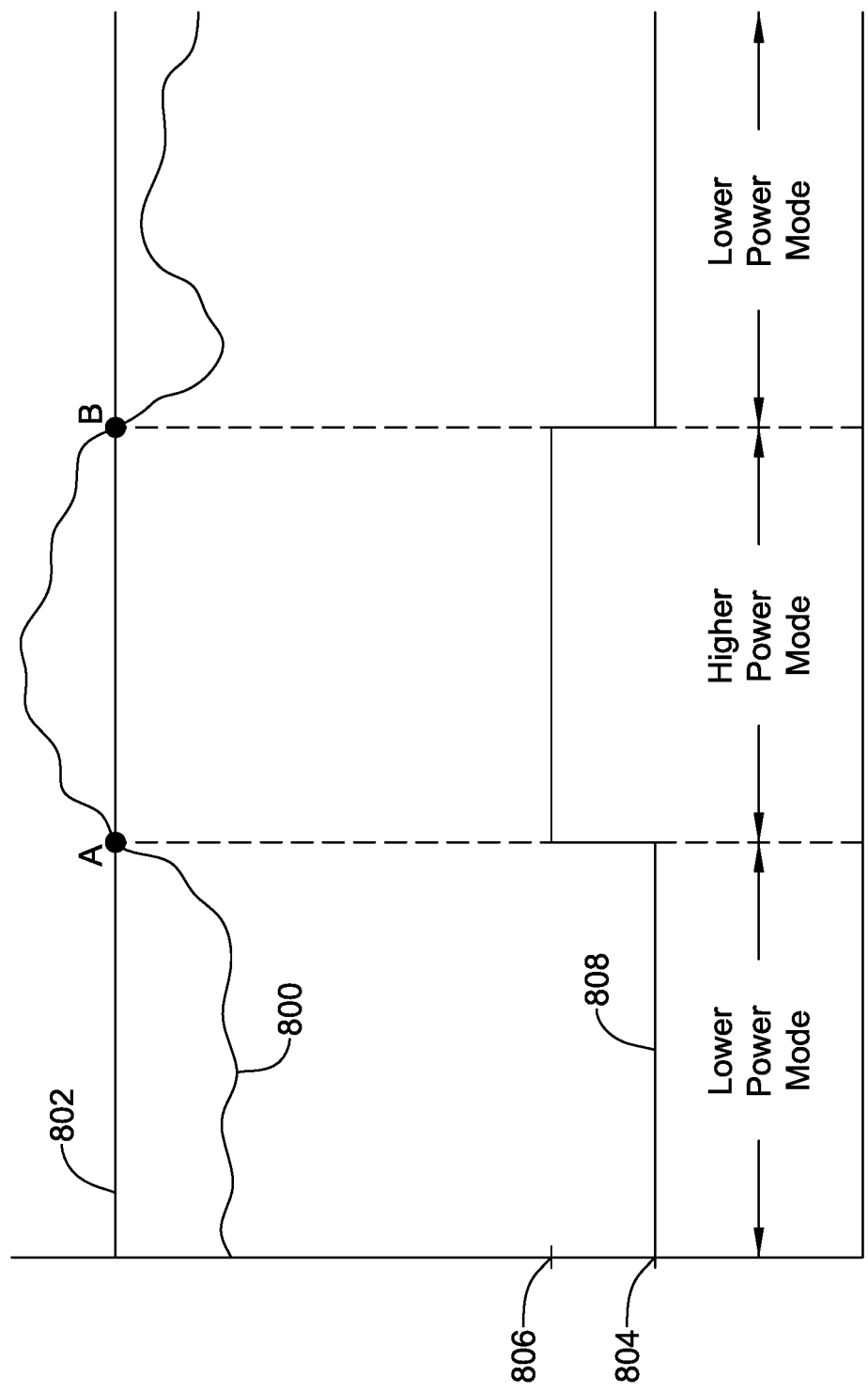
FIG. 8A is a timing diagram showing an illustrative operation of an LCP.

Turning specifically to FIG. 8A, a predetermined rule may specify that the receiver is to operate in the lower power mode when the output signal 800 is at or below the physiological parameter threshold 802, and the receiver is to operate in the higher power mode when the output signal 800 is above the physiological parameter threshold 802. As stated herein, in some cases, the output signal 800 may represent one or more sensed or determined physiological parameters such as heart rate, chamber pressure, PH levels, electrocardiogram (ECG) morphology, temperature (e.g., blood temperature, body tissue temperature, etc.), cardiac electrical signals, etc. In some examples, the cardiac electrical signals may represent local information from the chamber in which the LCP may be implanted. In some cases, the LCP may be configured to detect cardiac electrical signals from other chambers (e.g. far field), such as the P-wave from the atrium.

As shown in FIG. 8A, the output signal 800 is initially below the physiological parameter threshold 802. During this time, and in accordance with the illustrative rule, the receiver is placed in the lower power mode. In the lower power mode, the receiver may consume power at the first lower power level 804 as shown. Continuing with the example of FIG. 8A, at point A, the output signal 800 rises above the physiological parameter threshold 802. In accordance with the illustrative rule, the receiver is placed in the higher power mode. In the higher power mode, the receiver may consume power at the second higher power level 806 as shown. The receiver may remain in the higher power mode until the output signal 800 falls back below the physiological parameter threshold 802 at point B, where the receiver is placed back in the lower power mode. In the example shown, the physiological parameter threshold 802 is a fixed threshold. However, in some cases, the physiological parameter threshold 802 may be a threshold that may be variable, programmable, may be based on another sensed or determined the physiological parameter, and/or may be any other suitable threshold, as desired.

In another embodiment, also represented by FIG. 8A, the predetermined rule may specify that the receiver is to move from the lower power mode to the higher power mode when in the lower power mode when the LCP receives a valid telemetry command from an external device. In some cases, the external device may send a telemetry command when the output signal 800 rises above the physiological parameter threshold 802. In some cases, the command may be a command to deliver ATP therapy, post-shock pacing therapy, cardiac resynchronization therapy (CRT), etc. or other suitable therapy. In the lower power mode, the receiver may be capable of receiving communication from the external device, however, the receiver may consume between 0% and 90% of its maximum power level, between 5% and 75% of its maximum power level, below 80% of the maximum power level, below 60% of the maximum power level, below 50% of the maximum power level, below 30% of the maximum power level, below 20% of the maximum power level, below 10% of the maximum power level, or any other suitable level.

As shown in FIG. 8A, the output signal 800 is initially below the physiological parameter threshold 802. During this time the LCP has not received a telemetry command from the external device. In accordance with the illustrative rule, the receiver is placed in the lower power mode. In the lower power mode, the receiver may consume power at the first lower power level 804 as shown. Continuing with the example of FIG. 8A, at point A, the output signal 800 rises above the physiological parameter threshold 802 and communication is sent from the external device. In some cases, the LCP may determine if the communication is a valid telemetry command. If the communication is valid, in accordance with the illustrative rule, the receiver is placed in the higher power mode. In the higher power mode, the receiver may consume power at the second higher power level 806 as shown. Once the LCP executes the command and the output signal 800 falls back below the physiological parameter threshold 802 at point B, the receiver may be placed back in the lower power mode. In the example shown, the physiological parameter threshold 802 is a fixed threshold.

Figure 8B:
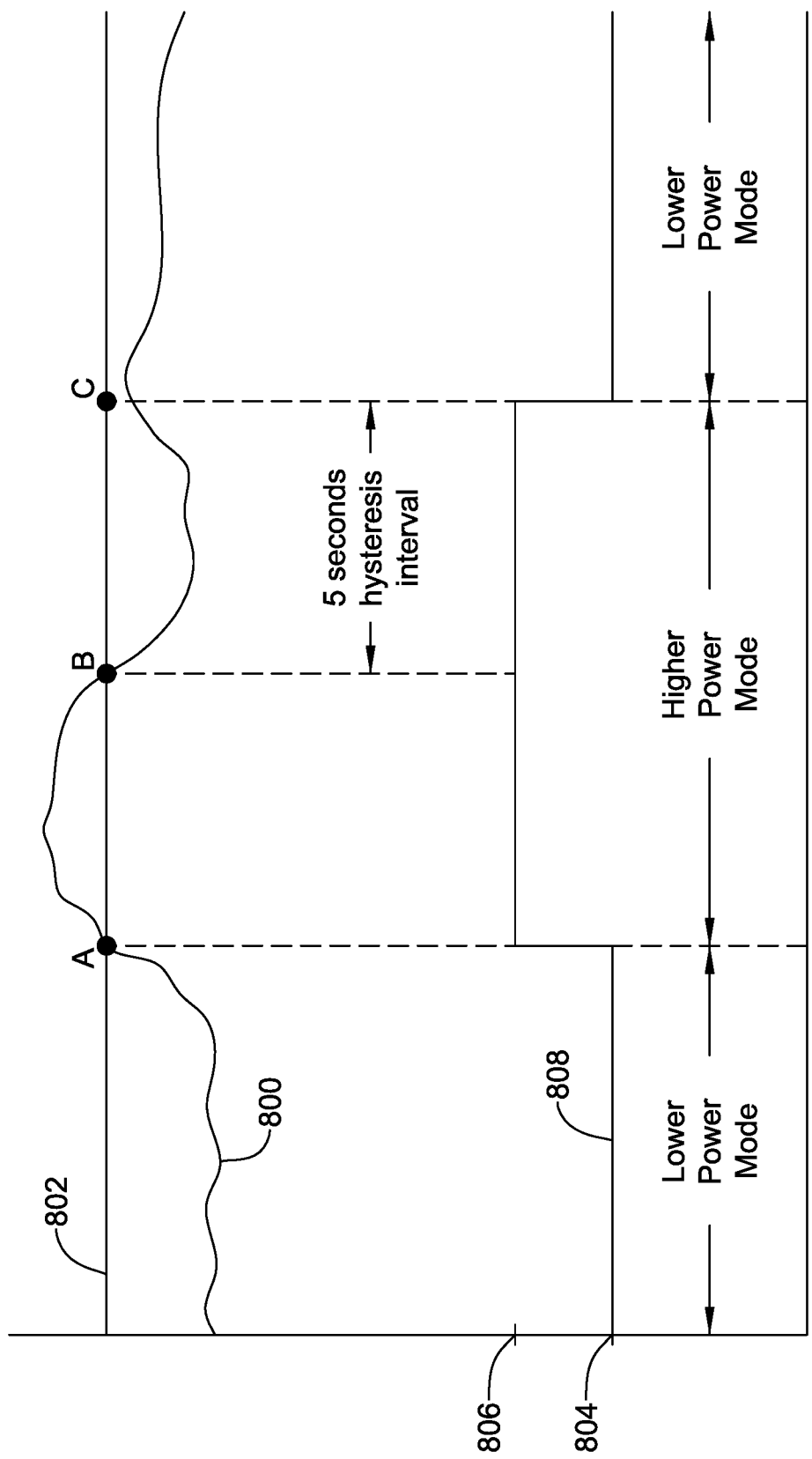
FIG. 8B is a timing diagram showing another illustrative operation of an LCP.

Turning now to the example shown in FIG. 8B. The example shown in FIG. 8B is the same as that shown in FIG. 8A, except in this case, the LCP may have a dynamic hysteresis or lag configured to wait 5 seconds before placing the receiver back in the lower power mode. For example, as shown in FIG. 8B, when the intrinsic heart rate goes from above the physiological parameter threshold 802 to below the physiological parameter threshold 802 at point B, the receiver remains at the higher power mode for 5 seconds before placing the receiver back into the lower power mode at point C. In some cases, this may allow enough time to determine that the patient's physiological parameter is going to remain below the physiological parameter threshold 802. In other examples, the dynamic hysteresis or lag may be 10 seconds, 30 seconds, 1 minute, 5 minutes, 10 minutes, 30 minutes, 1 hour, 5 hours, 10 hours, 24 hours, etc.

Figure 9:
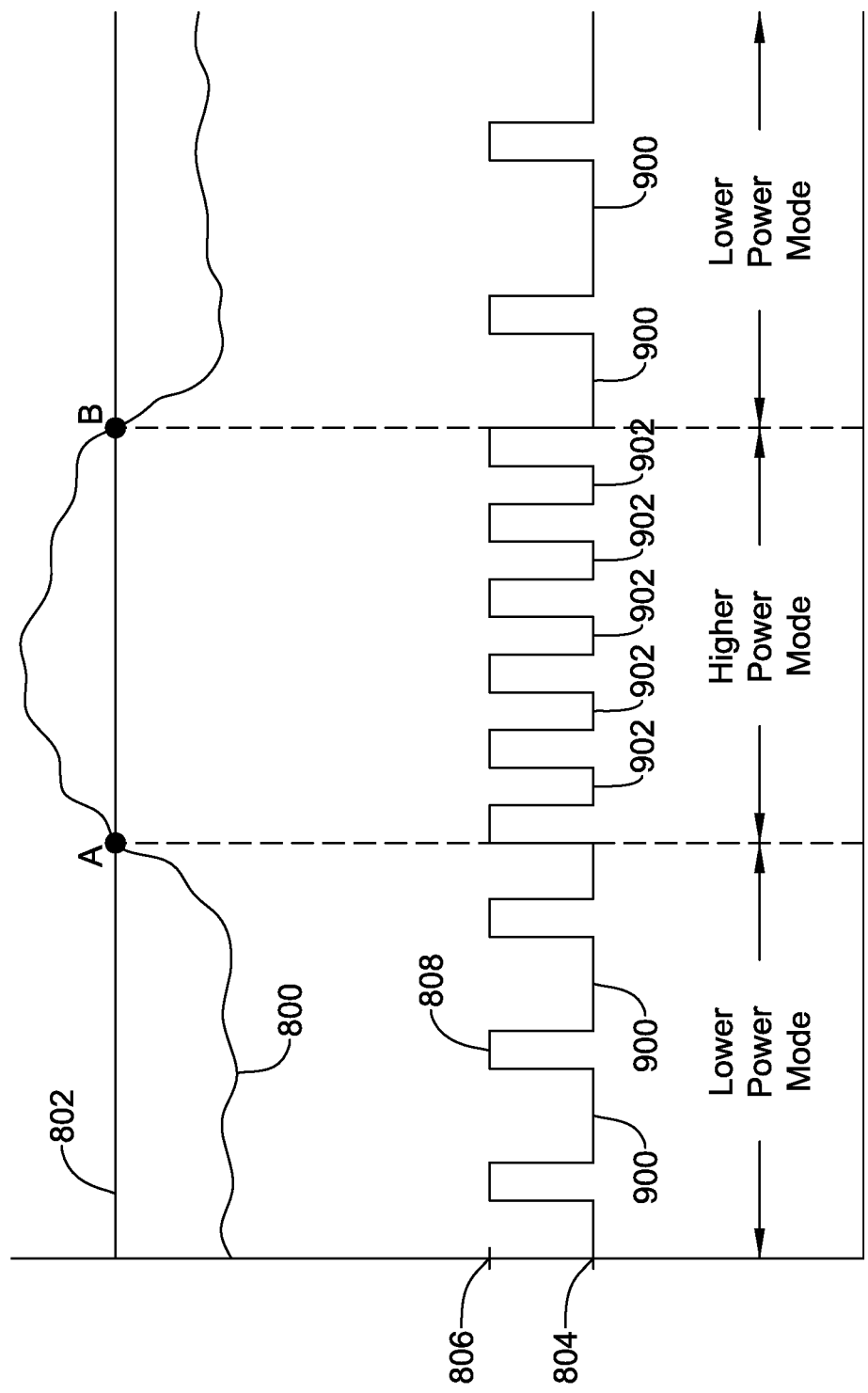
FIG. 9 is a timing diagram showing another illustrative operation of an LCP.

Turning now to the example shown in FIG. 9. The example shown in FIG. 9 is the same as that shown in FIG. 8, except that when the receiver is in the lower power mode, the receiver intermittently switches between the first lower power level 804 and the second higher power level 806 at a first rate and/or duty cycle, and when the receiver is in the higher power mode, the receiver intermittently switches between the first lower power level 804 and the second higher power level 806 at a second rate and/or duty cycle, wherein the second rate and/or duty cycle is higher (i.e. spends more time at the second higher power level 806) than the first rate and/or duty cycle. This may allow the receiver to receive communications while the receiver is in the lower power mode, but just with less bandwidth than when in the higher power mode.

Figure 10:
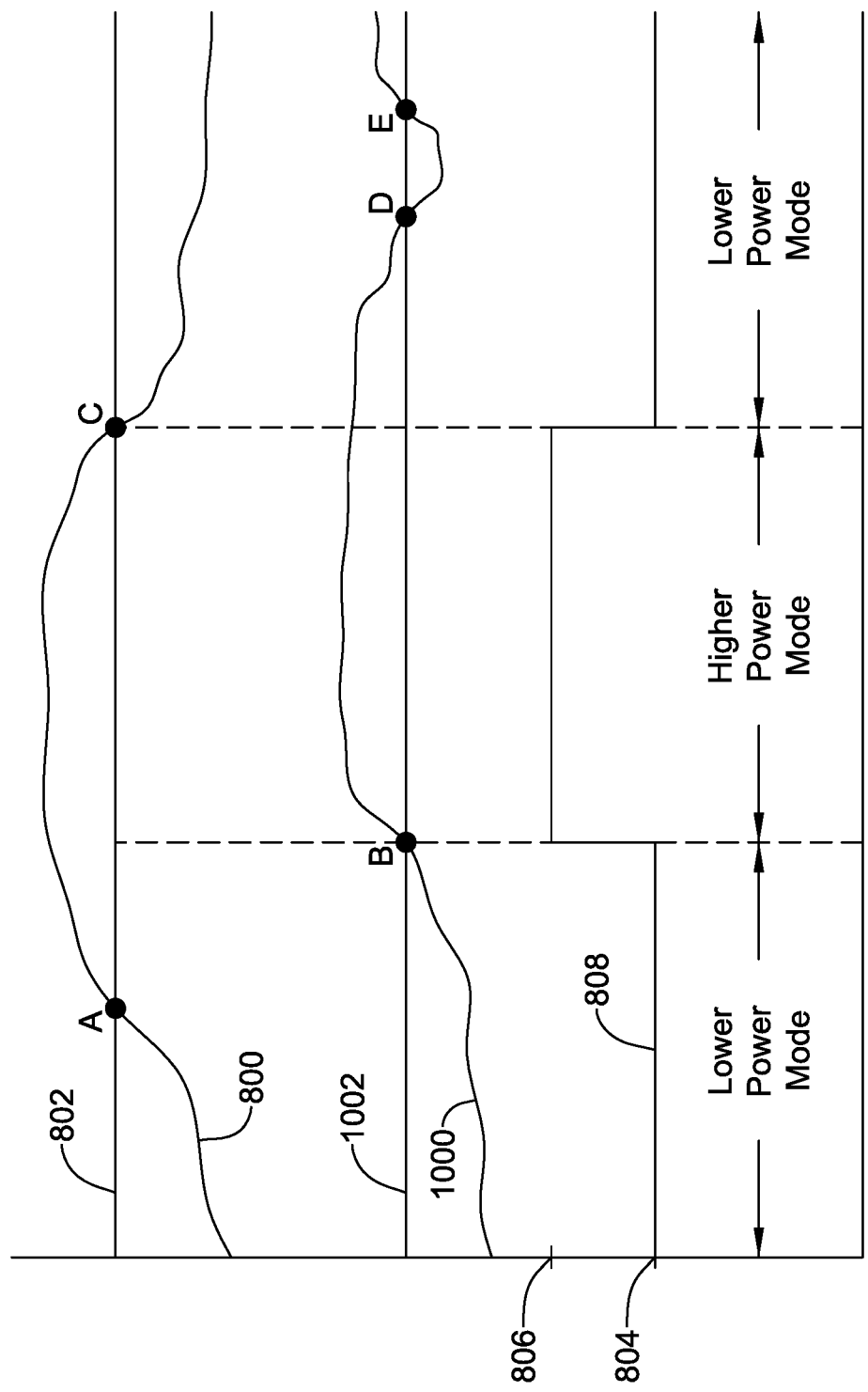
FIG. 10 is a timing diagram showing yet another illustrative operation of an LCP.

Turning now to FIG. 10, which shows the operation of a different rule. In FIG. 10, the rule specifies that the receiver is to operate in the lower power mode when a first output signal 800 is at or below a first physiological parameter threshold 802 "OR" a second output signal 1000 is at or below a second physiological parameter threshold 1002, and the receiver is to operate in the higher power mode when the first output signal 800 is above the first physiological parameter threshold 802 "AND" the second output signal 1000 is above the second physiological parameter threshold 1002.

Figure 11:
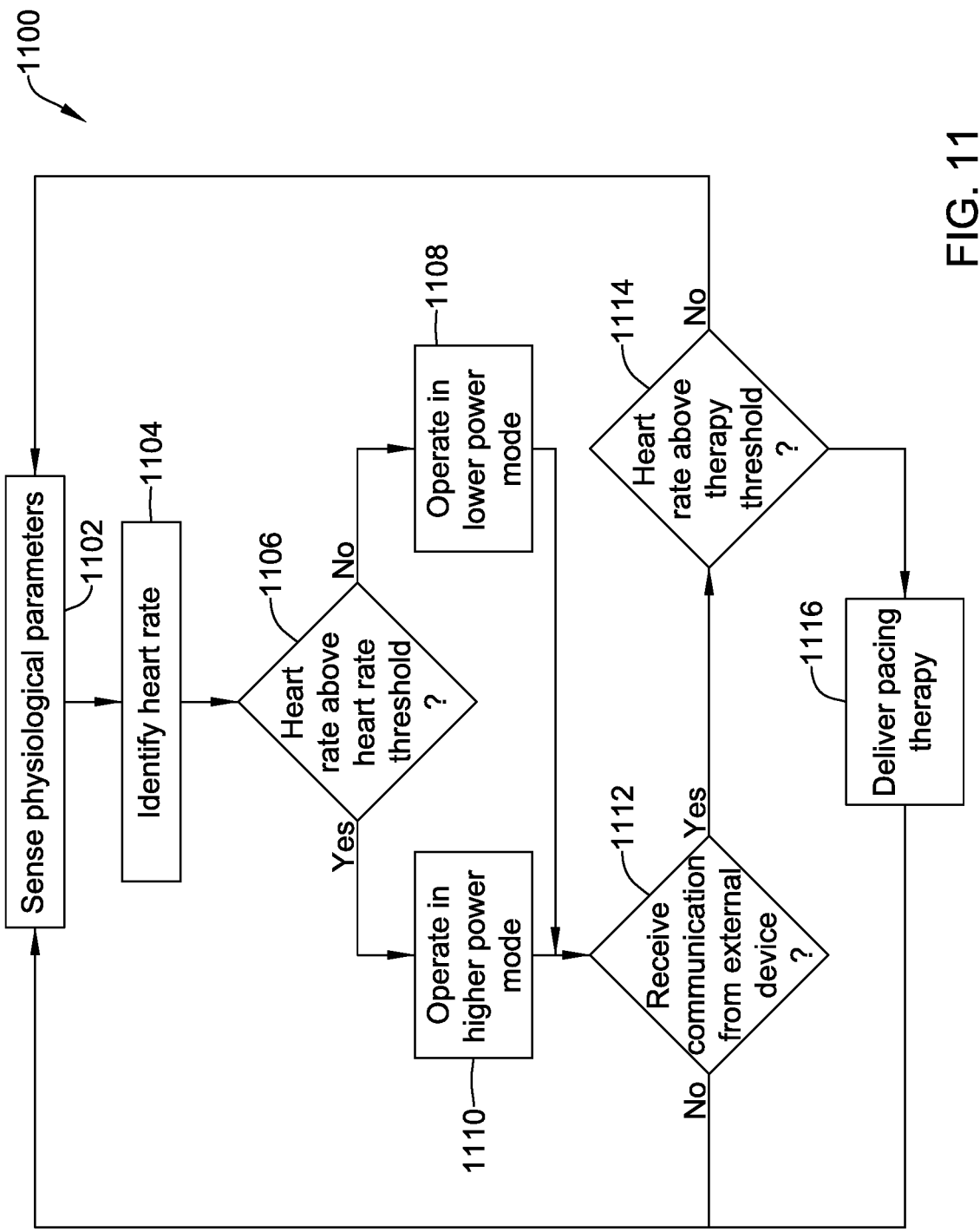
FIG. 11 is a flow diagram of an illustrative method that may be implemented by a medical device or medical device system, such as the illustrative medical devices and/or medical device systems shown in FIGS. 1-6.

FIG. 11 shows an example method 1100 of operation of an LCP configured to operate in two or more power modes or two or more power levels. In some cases, a rules based engine may be used to cause the receiver of the LCP to operate in a lower power mode or level if an intrinsic heart rate of a patient is at or below a heart rate threshold, and causes the receiver of the LCP to operate in a higher power mode or level if the intrinsic heart rate is above the heart rate threshold. Method 1100 begins at step 1102, where the LCP senses one or more physiological parameters of the patient. At step 1104, the LCP identify the intrinsic heart rate of the patient from the one or more sensed physiological parameters. At step 1106, the LCP may determine whether the intrinsic heart rate is above the heart rate threshold. If the intrinsic heart rate is not above the heart rate threshold, at step 1108, the LCP may operate its receiver in a lower power mode or level. In some cases, in the lower power mode or level, the receiver of the LCP may consume between 0% and 90% of its maximum power level, between 5% and 75% of its maximum power level, below 80% of the maximum power level, below 60% of the maximum power level, below 50% of the maximum power level, below 30% of the maximum power level, below 20% of the maximum power level, below 10% of the maximum power level, or any other suitable level. The heart rate threshold may be a fixed heart rate such as a rate limit, or may be a dynamic heart rate that is dependent on the activity level of the patient. In this configuration, the energy used to power the LCP may be conserved and potentially extend the operating life of the LCP. If the intrinsic heart rate is above the heart rate threshold, at step 1110, the LCP may operate its receiver in a higher power mode or level. In some cases, in the higher power mode or level, the LCP may operate at its maximum power level. While in the higher power mode or level or lower power mode or level, at step 1112, the LCP may determine whether a communication signal (e.g., a command to deliver pacing therapy) is received from the external device. If the communication signal is not received from the external device, the LCP may return to step 1102. If, however, the communication signal is received from the external device, at step 1114, the LCP may determine whether the intrinsic heart rate is above a therapy threshold. In some examples, the heart rate threshold and the therapy threshold may be the same. However, in other examples, the heart rate threshold and the therapy threshold may be different. If the LCP determines that the intrinsic heart rate is not above the therapy threshold, the LCP may return to step 1102. If, however, the LCP determines that the intrinsic heart is above the therapy threshold, at step 1116, the LCP may deliver demand pacing therapy (e.g., ATP therapy) to the patient.

Figure 12:
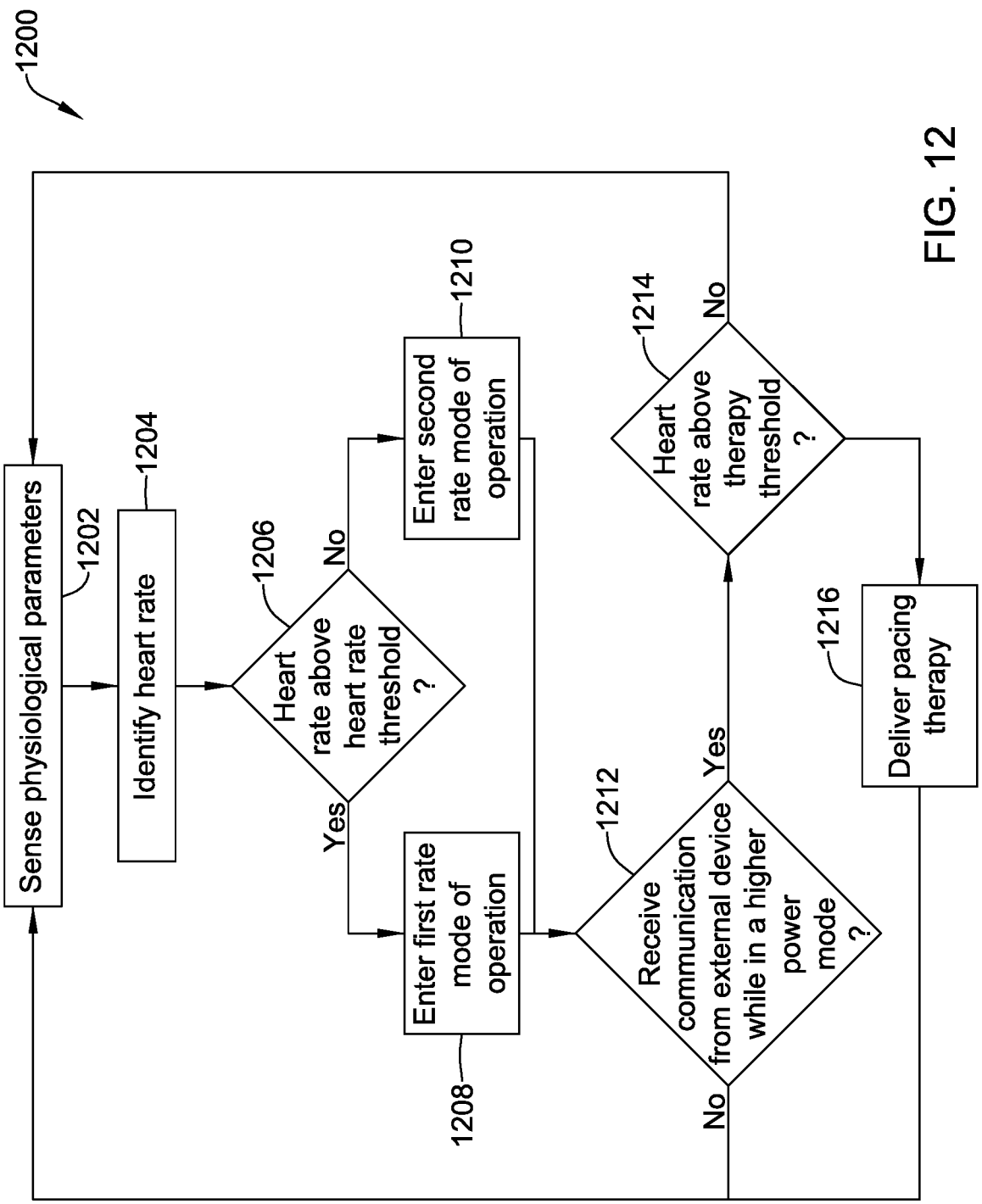
FIG. 12 is a flow diagram of another illustrative method that may be implemented by a medical device or medical device system, such as the illustrative medical devices and/or medical device systems shown in FIGS. 1-6.

FIG. 12 shows another example method 1200 of operation of an LCP configured to operate in two or more power modes or two or more power levels. In some cases, a rules based engine may be used to cause the receiver of the LCP to be intermittently placed in a higher power mode or level from a lower power mode or level more frequently over a period of time when an intrinsic heart rate is above a heart rate threshold than when the intrinsic heart rate value is below the heart rate threshold. Method 1200 begins at step 1202 where the LCP senses one or more physiological parameters of a patient. At step 1204, the LCP may identify the intrinsic heart rate from the one or more sensed physiological parameters. At step 1206, the LCP may determine whether the intrinsic heart rate is above the heart rate threshold. If the intrinsic heart rate is above the heart rate threshold, at step 1208, the LCP may operate in a first rate mode of operation where the receiver of the LCP is placed at a higher power level from a lower power level at a first rate frequency. If the intrinsic heart rate is not above the heart rate threshold, at step 1210, the LCP may operate in a second rate mode of operation where the receiver of the LCP is placed at the higher power level from the lower power level at a second rate frequency, where the second rate frequency is less than the first rate frequency. During the periods that the receiver of the LCP is at the lower power level, the receiver of the LCP may be incapable of communicating with an external device, and during the periods that the receiver of the LCP is at the higher power level, the receiver of the LCP may be capable of communicating with an external device. In some cases, in the first rate mode of operation, the receiver of the LCP may consume between 0% and 90% of its maximum power level, between 5% and 75% of its maximum power level, below 80% of the maximum power level, below 60% of the maximum power level, below 50% of the maximum power level, below 30% of the maximum power level, below 20% of the maximum power level, below 10% of the maximum power level, or any other suitable level.

At step 1212, if the LCP is in the higher power mode or level, the LCP may determine whether a communication signal (e.g., a command to deliver pacing therapy) is received from the external device. If the communication signal is not received from the external device, the LCP may return to step 1202. If, however, the communication signal is received from the external device, at step 1214, the LCP may determine whether the intrinsic heart rate is above a therapy threshold. In some examples, the heart rate threshold and the therapy threshold may be the same. However, in other examples, the heart rate threshold and the therapy threshold may be different. If the LCP determines that the intrinsic heart rate is not above the therapy threshold, the LCP may return to step 1202. If, however, the LCP determines that the intrinsic heart is above the therapy threshold, at step 1216, the LCP may deliver demand pacing therapy (e.g., ATP therapy) to the patient.

Figure 13:
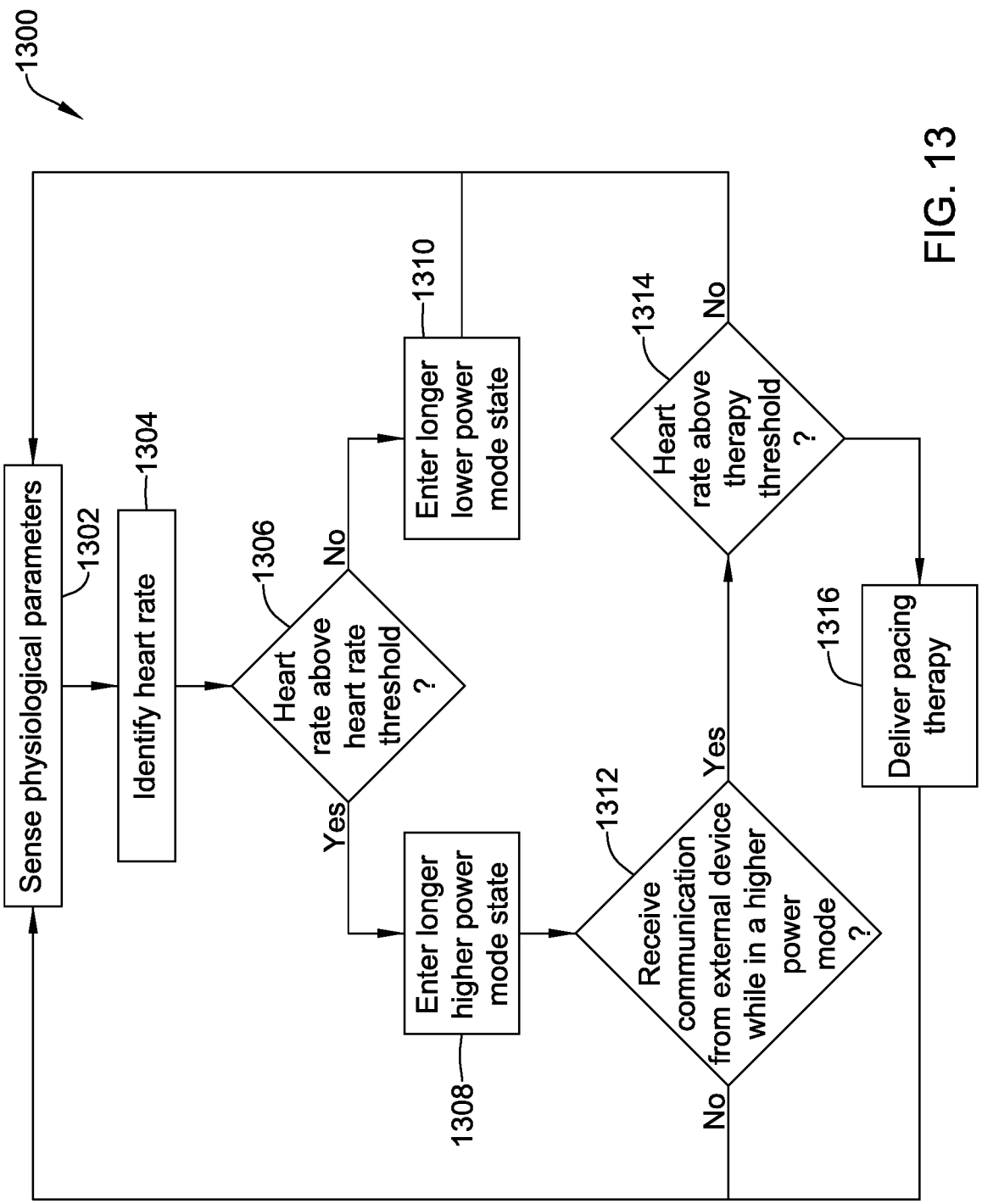
FIG. 13 is a flow diagram of another illustrative method that may be implemented by a medical device or medical device system, such as the illustrative medical devices and/or medical device systems shown in FIGS. 1-6.

FIG. 13 shows another example method 1300 of operation of an LCP configured to operate in two or more power modes or two or more power levels. In some cases, a rules based engine may be used to cause the receiver of the LCP to be placed in a higher power mode or level for a longer period of time than a lower power mode or level time when an intrinsic heart rate value is above a heart rate threshold than when the intrinsic heart rate value is below the heart rate threshold. Method 1300 begins at step 1302 where the LCP senses one or more physiological parameters of a patient. At step 1304, the LCP may identify the intrinsic heart rate from one or more of the sensed physiological parameters. At step 1306, the LCP may determine whether the intrinsic heart rate is above the heart rate threshold. If the intrinsic heart rate is above the heart rate threshold, at step 1308, the LCP may operate its receiver in the higher power mode or level for a longer period of time than the lower power mode or level than when the intrinsic heart rate is not above the heart rate threshold. If the intrinsic heart rate is below the heart rate threshold, and at step 1310, the LCP may operate its receiver in the lower power mode or level for a longer period of time than the higher power mode or level. During the periods that the LCP is in the lower power mode or level, the LCP may be incapable of communicating with an external device. During the periods that the LCP is in the higher power mode or level, the LCP may be capable of communicating with an external device. In some cases, when the LCP operates its receiver in the lower power mode or level for a longer period of time than the higher power mode or level, the receiver of the LCP may consume between 0% and 90% of its maximum power level, between 5% and 75% of its maximum power level, below 80% of the maximum power level, below 60% of the maximum power level, below 50% of the maximum power level, below 30% of the maximum power level, below 20% of the maximum power level, below 10% of the maximum power level, or any other suitable level.

At step 1312, if the LCP is in the higher power mode or level, the LCP may determine whether a communication signal (e.g., a command to deliver pacing therapy) is received from the external device. If the communication signal is not received from the external device, the LCP may return to step 1302. If, however, the communication signal is received from the external device, at step 1314, the LCP may determine whether the intrinsic heart rate is above a therapy threshold. In some examples, the heart rate threshold and the therapy threshold may be the same. However, in other examples, the heart rate threshold and the therapy threshold may be different. If the LCP determines that the intrinsic heart rate is not above the therapy threshold, the LCP may return to step 1302. If, however, the LCP determines that the intrinsic heart is above the therapy threshold, at step 1316, the LCP may deliver demand pacing therapy (e.g., ATP therapy) to the patient.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Also, in the above Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An implantable medical device (IMD) comprising:
   a controller;
   a receiver having a higher power mode and a lower power mode, wherein:
      in the higher power mode, the receiver can receive a communication from an external device and pass the received communication to the controller;
      in the lower power mode, the receiver cannot receive the communication from the external device and the IMD is configured to operate independently of the external device;
   a physiological sensor providing an output to the controller; and
   wherein the controller is configured to:
      identify a physiological parameter value based on the output of the physiological sensor, the physiological parameter value including a heart rate value;
      based on one or more rules conditioned at least in part on the identified physiological parameter value, control whether the receiver is in the higher power mode or the lower power mode; and
      wherein when the one or more rules specify that the receiver is to be placed in the higher power mode, the receiver is intermittently switched between a higher power level and a lower power level and spends relatively more time at the higher power level, and when the receiver is to be placed in the lower power mode, the receiver is intermittently switched between the higher power level and the lower power level and spends relatively more time at the lower power level.

2. The IMD according to claim 1, wherein the communication from the external device comprises a signal and the controller is further configured to control whether the receiver is in the higher power mode or the lower power mode based at least in part on the signal.

3. The IMD according to claim 1, wherein the implantable medical device is configured to receive a command from the external device when the receiver is in the higher power mode and the implantable medical device is configured to use a hysteresis function when switching from the higher power mode to the lower power mode.

4. The IMD according to claim 1, wherein the one or more rules specify that the receiver is to be placed in the higher power mode when the heart rate value is above a heart rate threshold and the receiver is to be placed in the lower power mode when the heart rate value is below the heart rate threshold.

5. The IMD according to claim 1, wherein when the one or more rules specify that the receiver is to be placed in the higher power mode, the receiver is intermittently switched between the higher power level and the lower power level at a first rate,
   and when the receiver is to be placed in the lower power mode, the receiver is intermittently switched between the higher power level and the lower power level at a second rate, wherein the first rate is higher than the second rate.

6. The IMD according to claim 1, wherein the identified physiological parameter value further includes one of a PH value, a potassium level, a glucose level, an ammonium level, a temperature value, a respiration rate, a ECG morphology value, an accelerometer value, a posture of a patient, a time of day.

7. The IMD according to claim 1, wherein the implantable medical device is a leadless cardiac pacemaker (LCP).

8. A leadless cardiac pacemaker (LCP) comprising:
   a housing;
   one or more physiological sensors for sensing one or more physiological parameters of a patient;
   two or more electrodes at least two of which for delivering pacing pulses to a heart of the patient;
   a receiver disposed within the housing and configured to operate in a lower power mode and a higher power mode, wherein:
      in the higher power mode, the receiver can receive an ATP command from an external device;
      in the lower power mode, the receiver cannot receive the ATP command from the external device;
   operational circuitry operatively coupled to the one or more physiological sensors, the two or more electrodes, and the receiver, the operational circuitry configured to:
      switch the receiver between the lower power mode and the higher power mode based at least in part on a heart rate of the patient determined at least in part on one or more physiological parameters sensed by one or more of the physiological sensors; and
      deliver anti-tachyarrhythmia pacing (ATP) therapy via two or more of the electrodes in response to the receiver receiving an ATP command from the external device when the receiver is in the higher power mode; and not receiving an ATP command from the external device when the receiver is in the lower power mode, and thus not delivering ATP therapy via the two or more electrodes.

9. The LCP of claim 8, wherein the operational circuitry is configured to:
place the receiver in the higher power mode when the heart rate exceeds an ATP heart rate threshold; and
place the receiver in the lower power mode when the heart rate does not exceed the ATP heart rate threshold.

10. The LCP of claim 8, wherein the operational circuitry is configured to:
switch the receiver to the higher power mode when the heart rate exceeds a heart rate threshold, and in the higher power mode, the receiver is switched back and forth between a higher power level and a lower power level and spends relatively more time at the higher power level; and
switch the receiver to the lower power mode when the heart rate does not exceed the heart rate threshold, and in the lower mode power, the receiver is switched back and forth between the higher power level and the lower power level and spends relatively more time at the lower power level.

11. The LCP of claim 8, wherein the one or more physiological sensors comprise two or more of the electrodes.

12. The LCP of claim 11, wherein the one or more physiological sensors comprises one or more cardiac electrical sensors, and the one or more physiological parameters comprise one or more electrical signals produced by the one or more cardiac electrical sensors.

13. The LCP of claim 8, wherein the one or more physiological sensors comprise a mechanical sensor, and the one or more physiological parameters comprise one or more mechanical signals produced by the mechanical sensor.

14. A leadless cardiac pacemaker (LCP) comprising:
a housing;
one or more physiological sensors for sensing one or more physiological parameters of a patient;
two or more electrodes for delivering pacing pulses to a heart of the patient;
a receiver with an adjustable power level;
electronics operatively coupled to the one or more physiological sensors, the two or more electrodes, and the receiver, the electronics is configured to:
adjust the receiver between a lower power level and a higher power level based at least in part on the one or more of the physiological parameters sensed by one or more of the physiological sensors, wherein:
in the higher power level, the receiver can receive a command from an external device;
in the lower power level, the receiver cannot receive the command from the external device; and
operate the LCP independently of the external device when the receiver is at the lower power level.

15. The LCP according to claim 14, wherein the LCP is configured to operate in cooperation with the external device, at least at times when the receiver is at the higher power level.

16. The LCP according to claim 15, wherein the LCP is configured to operate in accordance with a command received from the external device when the receiver is at the higher power level.

17. The LCP according to claim 16, wherein the command is an ATP trigger command.

* * * * *